(12) United States Patent
Chen

(10) Patent No.: US 7,385,103 B2
(45) Date of Patent: Jun. 10, 2008

(54) ANIMAL MODEL, CELLS, AND TREATMENT FOR MALIGNANT MELANOMA

(75) Inventor: Suzie Chen, Highland Park, NJ (US)

(73) Assignee: Rutgers, the State University, New Brunswick, NJ (US)

( * ) Notice: Subject to any disclaimer, the term of this patent is extended or adjusted under 35 U.S.C. 154(b) by 17 days.

(21) Appl. No.: 11/091,076

(22) Filed: Mar. 28, 2005

(65) Prior Publication Data

US 2005/0235366 A1    Oct. 20, 2005

Related U.S. Application Data

(60) Provisional application No. 60/649,022, filed on Feb. 1, 2005, provisional application No. 60/563,131, filed on Apr. 16, 2004.

(51) Int. Cl.
*A01K 67/027* (2006.01)
*A01K 67/00* (2006.01)

(52) U.S. Cl. ............................. 800/18; 800/13; 800/14

(58) Field of Classification Search .................... None
See application file for complete search history.

(56) References Cited

U.S. PATENT DOCUMENTS 5,869,609 A    2/1999    Mulvihill et al. ........... 530/350

OTHER PUBLICATIONS

MacKenzie, MA et al. Dev Biol 192:99-107, 1997.*
Bonilla, R et al. FASEB J. (4-5):abstract No. 468.23, Mar. 2003.*
Pollock, PM et al. Nature Genet 34:108-112, May 2003.*
Sigmund, CD. Arterioscler Thromb Vasc Biol. 20:1425-1429, 2000.*
Cameron, ER. Molec Biotech 7:253-265, 1997.*
Mullins, JJ and LJ Mullins. Hypertension 22:630-633, 1993.*
Niemann, H. Trans Research 7:73-75, 1998.*
Kappel, CA et al. Curr Opin Biotech 3:548-553, 1992.*
Mullins, LJ and JJ Mullins. J Clin Invest 98(11):S37-S40, 1996.*
Houdebine, LM. J Biotech 34:269-287, 1994.*
Wall, RJ. Theriogenology 45:57-68, 1996.*
Aiba et al., "Reduced Hippocampal Long-Term Potentiation and Context-Specific Deficit in Associative Learning in mGluR1 Mutant Mice", Cell 1994 79:365-375.
Aiba et al., "Deficient Cerebellar Long-Term Depression and Impaired Motor Learning in mGluR1 Mutant Mice", Cell 1994 79:377-388.
Chen et al., "Spontaneous Melanocytosis in Transgenic Mice", J. Invest. Dermatol. 1996 106:1145-1151.
Cohen-Solal et al., "Development of Cutaneous Amelanotic Melanoma in the Absence of a Functional Tyrosinase", Pigment Cell Res 2001 14:466-474.
Colon-Teicher et al., "Genomic sequences capable of committing mouse and rat fibroblasts to adipogenesis", Nucleic Acids Research 1993 21(9) :2223-2228.
Conquet et al., "Motor deficit and impairment of synaptic plasticity in mice lacking mGluR1", nature 1994 372:237-243.
Skerry et al., "Glutamate signalling in non-neuronal tissues", TRENDS in Pharmacological Sciences 2001 22(4) :174-181.
Zhu et al., "Development of Heritable Melanoma in Transgenic Mice", J. Invest. Dermatol. 1998 110:247-252.

* cited by examiner

*Primary Examiner*—Peter Paras, Jr.
*Assistant Examiner*—Marcia S Noble
(74) *Attorney, Agent, or Firm*—Licata & Tyrrell PC

(57) ABSTRACT

The present invention provides transgenic non-human animal models and cell lines which express a metabotropic glutamate receptor 1 in a melanocyte-specific manner and, as a result, exhibit a predisposition to the development of melanoma. The invention further teaches methods of using the transgenic animals and cell lines to identify therapeutic agents. Diagnostic methods for detecting a melanoma are also provided.

1 Claim, No Drawings

SEQUENCE LISTING

```
<160> NUMBER OF SEQ ID NOS: 15

<210> SEQ ID NO 1
<211> LENGTH: 4237
<212> TYPE: DNA
<213> ORGANISM: Mus musculus

<400> SEQUENCE: 1
cccagatggc agccttgcac cgtctgattt ggagctgagg tgtctgcgaa ccgagggcgg      60
ctgcagtcct ctgacctgag accaatagct ctgtctaccc ggactcagcg tccagcttat     120
ggccactaac gcgccgctca ttgcacacct gattcacaca ccttcgggca ccagtgaaaa     180
aaccgcgact tgattttctg gaagaacacc cctagggttt gggagcggtc gtggaggacc     240
agcaggaaga agcggagggg agaggggcgg tggtggagac tgagaagctt tgaaccagct     300
gtgttggcca aaggcacgaa gcggcaaaag acagcggcgg gcgtcagggt ggttcgcgct     360
gggaacctgc aggcgggacc ggcgtgggaa cgtggcttgc cggcggtcga ccgcgtcttc     420
gccacaatgg tccggctcct cttgattttc ttcccaatga tcttttttgga gatgtccatt     480 ttgcccagga tgcctgacag aaaagtactg ctggcaggtg cctcgtccca gcgctctgtg     540
gcgagaatgg acggagatgt catcatcgga gccctcttct cagtccatca ccagcctcca     600
gccgaaaagg taccggaaag gaagtgtggg gagatcagag aacagtatgg tatccagaga     660
gtggaggcca tgttccacac attagataag attaatgcgg acccggtgct cctgcccaac     720
atcactctgg gcagtgagat ccgggactcc tgctggcact cttctgtggc tctgaacag     780 agcattgagt tcatcagaga ctccctgatt tccatccgag atgagaagga tggactgaac     840
cgctgcctgc ctgatggcca gaccctaccc ccaggcagga ctaagaagcc tattgctgga     900
gtgatcggcc ctggctccag ctctgtggcc attcaagtcc agaatcttct gcagctgttc     960
gacatcccac aaatcgccta ttctgccacg agcatagacc tgagcgacaa aactttgtac    1020
aaatacttcc tgagggtggt cccttctgac actttgcagg caagggcgat gcttgatatc    1080
gtcaagcggt acaactggac ctatgtctct gcagtccaca cagaagggaa ttacggcgag    1140
agtggaatgg atgctttcaa agagttggct gcccaggaag gactctgcat cgcacactcg    1200
gacaaaatct acagcaatgc tggcgagaag agctttgatc ggcttctgcg caagctccga    1260
gagcggcttc ccaaggccag ggttgtggtc tgcttctgcg agggcatgac agtgcggggg    1320
ttactgagtg ccatgcgccg ccttggcgtc gtgggagagt tctcactcat tggaagtgat    1380
ggatgggcag acagagatga agtcatcgaa ggctatgagg tggaagccaa tgggggaatc    1440
acaataaagc tgcagtctcc agaggtcagg tcgtttgatg actactttct gaagctgagg    1500
```

-continued

```
ctggacacca acacgaggaa tccttggttc cctgagttct ggcaacatcg cttccagtgt    1560
cgcctacctg gacacctctt ggaaaacccc aactttaaaa aagtctgcac aggaaatgaa    1620
agcttggaag aaaattatgt ccaggacagc aaaatgggat ttgtcatcaa cgccatctat    1680
gccatggcac acggcctaca gaacatgcac catgctctat gtcctggcta cgtgggcctt    1740
tgtgatgcca tgaagcccat tgacggcagg aagctcctgg atttcctcat caaatcctct    1800
tttgttggag tgtctggaga ggaggtctgg ttcgatgaga aggggatgc acctggaagg     1860 tatgacatta tgaatctgca gtacacagag gctaatcgct atgactatgt ccatgtggga    1920
acctggcatg aaggtgtgct gaatatcgat gattacaaaa tccagatgaa caaaagcgga    1980
atggtacgat ctgtgtgcag cgagccttgc ttaaagggtc agattaaggt catacggaaa    2040
ggggaagtga gctgctgctg gatctgcaca gcctgcaaag agaatgagtt tgtgcaagat    2100
gagtttacct gcagagcctg tgacctgggg tggtggccca atgcagagct cacaggctgt    2160
gagcccatta ctatccgtta cctcgagtgg agtgacatag aatccatcat agccatcgcc    2220
ttttcttgcc tgggcatcct cgtgacgcta tttgtcaccc tcatctttgt gctgtaccgg    2280
gacacacctg tggtcaaatc ctccagtaga gagctctgct atatcattct ggctggtatt    2340
ttcctcggct acgtatgccc tttcaccctc atcgccaaac ctactaccac atcctgctac    2400
ctccagcgcc tcctagttgg cctctcttct gccatgtgct actctgctct tgtgaccaaa    2460
accaatcgta ttgcacgcat cctggctggc agcaagaaga gatctgtac ccggaagccc     2520 aggttcatga gcgcttgggc ccaagtgatc atagcctcca ttctgattag tgtacagctg    2580
acactagtgg tgaccttgat catcatggag cctcccatgc ccattttgtc ctacccgagc    2640
atcaaggaag tctatcttat ctgcaatacc agcaacctgg gtgtagtggc acctgtgggt    2700
tacaacggac ttctcatcat gagctgtacc tactatgcct tcaagacccg caacgtgccg    2760
gccaatttca tgaggctaa atacatcgcc ttcactatgt acaccacctg catcatctgg    2820
ctggcttttg ttcccattta ctttgggagc aactacaaga ttatcactac ctgcttcgca    2880
gtgagcctca gtgtgacggt ggccctgggc tgcatgttca ctcccaagat gtacatcatt    2940
attgccaaac ccgagaggaa tgtccgcagt gccttcacca cctctgatgt agtgcgcatg    3000
cacgtcggtg acggcaagct gccatgccgc tccaacacct tcctcaacat tttccggaga    3060
aagaagcctg gggcagggaa cgccaattct aacggcaagt ctgtgtcatg gtctgaacca    3120
ggtggaagac aggcgcccaa gggacagcat gtgtggcagc cctctctgt gcacgtgaag    3180 accaatgaga cggcctgtaa ccaaacagcc gtaattaaac ccctcactaa aagttaccaa    3240
ggctctggca agagtctgac cttttcagac gccagcacca agaccccttta caacgtggag    3300 gaagaggaca ataccccttc aactcacttc agccctccca gcagcccttc catggtggtg    3360
caccgacgcg ggccacccgt ggccaccacg ccacctctgc caccccacct tagcgcagaa    3420
gagacgccct tgttcctggc tgattctgtc atccccaagg gcttgcctcc tcctctcccg    3480
cagcagcaac agcagccgcc ccctcagccg cctccgcagc agcccaaatc cctgatggac    3540
cagctgcaag gcgtggtcac caactttggc tctgggattc cagacttcca cgcggtgctg    3600
gcaggcccgg ggacaccagg gaacgggctg cgctccctgt acccgccccc gcctccaccg    3660
caacacctgc agatgttgcc cctgcagctg agcaccttcc gagaggagcc catctcccct    3720 ccggggagg acgacgatga tgacagcagc gagaggttca gctcctgca ggagttcgtg     3780 tatgagcgtg aagggaacac ggaggaagac gatctggaag aggaggagga cctgcctgca    3840
```

-continued

| | |
|---|---:|
| gccagcaagc tgacgcctga ggattcgcct gccctgacgc cccttctcc tttccgagat | 3900 |
| tccgtggcct ctggcagctc agtgcccagt tccccagtgt ctgagtcagt gctctgcacc | 3960 |
| cctccaaatg tgacctatgc ctctgtcatt ctgagggact acaagcaaag ctcttccact | 4020 |
| ctgtagtaag gggggagtat gcgtggagaa gccagagatg ccaaggagtg tcaaccctt | 4080 |
| cagaaatgtg tagaaagcaa gggggtgggg tgggatggag gaccacagtc tgcagggaag | 4140 |
| aaaaaaaga aaggaaaagg aaaggaaagg aaaggaaagg aaaggaaagg aaaggaaagg | 4200 |
| aaaggaaagg aaaggaaagg aaaggaaagg aaaaaa | 4237 |

<210> SEQ ID NO 2
<211> LENGTH: 6619
<212> TYPE: DNA
<213> ORGANISM: Homo sapiens

<400> SEQUENCE: 2

| | |
|---|---:|
| gaattccctt acaaacgcct ccagcttgta gaggcggtcg tggaggaccc agaggaggag | 60 |
| acgaagggga aggaggcggt ggtggaggag gcaaaggcct tggacgacca ttgttggcga | 120 |
| ggggcaccac tccgggagag gcggcgctgg gcgtcttggg ggtgcgcgcc gggagcctgc | 180 |
| agcgggacca gcgtgggaac gcggctggca ggctgtggac ctcgtcctca ccaccatggt | 240 |
| cgggctcctt ttgttttttt tcccagcgat cttttggag gtgtcccttc tcccagaag | 300 |
| ccccggcagg aaagtgttgc tggcaggagc gtcgtctcag cgctcggtgg ccagaatgga | 360 |
| cggagatgtc atcattggag ccctcttctc agtccatcac cagcctccgg ccgagaaagt | 420 |
| gcccgagagg aagtgtgggg agatcaggga gcagtatggc atccagaggg tggaggccat | 480 |
| gttccacacg ttggataaga tcaacgcgga ccccggtcctc ctgcccaaca tcaccctggg | 540 |
| cagtgagatc cgggactcct gctggcactc ttccgtggct ctgaacaga gcattgagtt | 600 |
| cattagggac tctctgattt ccattcgaga tgagaaggat gggatcaacc ggtgtctgcc | 660 |
| tgacggccag tccctccccc caggcaggac taagaagccc attgcgggag tgatcggtcc | 720 |
| cggctccagc tctgtagcca ttcaagtgca gaacctgctc cagctcttcg acatccccca | 780 |
| gatcgcttat tcagccacaa gcatcgacct gagtgacaaa actttgtaca aatacttcct | 840 |
| gagggttgtc ccttctgaca cttttgcagg caagggccatg cttgacatag tcaaacgtta | 900 |
| caattggacc tatgtctctg cagtccacac ggaagggaat tatggggaga gcggaatgga | 960 |
| cgctttcaaa gagctggctg cccaggaagg cctctgtatc gcccattctg acaaaatcta | 1020 |
| cagcaacgct ggggagaaga gctttgaccg actcttgcgc aaactccgag agaggcttcc | 1080 |
| caaggctaga gtggtggtct gcttctgtga aggcatgaca gtgcgaggac tcctgagcgc | 1140 |
| catgcggcgc cttggcgtcg tggcgagtt ctcactcatt ggaagtgatg gatgggcaga | 1200 |
| cagagatgaa gtcattgaag gttatgaggt ggaagccaac gggggaatca cgataaagct | 1260 |
| gcagtctcca gaggtcaggt catttgatga ttatttcctg aaactgaggc tggacactaa | 1320 |
| cacgaggaat ccctggttcc ctgagttctg gcaacatcgg ttccagtgcc gccttccagg | 1380 |
| acaccttctg gaaaatccca actttaaacg aatctgcaca ggcaatgaaa gcttagaaga | 1440 |
| aaactatgtc caggacagta agatggggtt tgtcatcaat gccatctatg ccatggcaca | 1500 |
| tgggctgcag aacatgcacc atgccctctg ccctggccac gtgggcctct gcgatgccat | 1560 |
| gaagcccatc gacggcagca agctgctgga cttcctcatc aagtcctcat tcattggagt | 1620 |
| atctggagag gaggtgtggt ttgatgagaa aggagacgct cctggaaggt atgatatcat | 1680 |
| gaatctgcag tacactgaag ctaatcgcta tgactatgtg cacgttggaa cctggcatga | 1740 |

```
aggagtgctg aacattgatg attacaaaat ccagatgaac aagagtggag tggtgcggtc    1800
tgtgtgcagt gagccttgct taaagggcca gattaaggtt atacggaaag gagaagtgag    1860
ctgctgctgg atttgcacgg cctgcaaaga gaatgaatat gtgcaagatg agttcacctg    1920
caaagcttgt gacttgggat ggtggcccaa tgcagatcta acaggctgtg agcccattcc    1980
tgtgcgctat cttgagtgga gcaacatcga atccattata gccatcgcct tttcatgcct    2040
gggaatcctt gttaccttgt ttgtcaccct aatctttgta ctgtaccggg acacaccagt    2100
ggtcaaatcc tccagtcggg agctctgcta catcatccta gctggcatct tccttggtta    2160
tgtgtgccca ttcactctca ttgccaaacc tactaccacc tcctgctacc tccagcgcct    2220
cttggttggc ctctcctctg cgatgtgcta ctctgcttta gtgactaaaa ccaatcgtat    2280
tgcacgcatc ctggctggca gcaagaagaa gatctgcacc cggaagccca ggttcatgag    2340
tgcctgggct caggtgatca ttgcctcaat tctgattagt gtgcaactaa ccctggtggt    2400
aaccctgatc atcatggaac ccctatgcc cattctgtcc tacccaagta tcaaggaagt    2460
ctaccttatc tgcaatacca gcaacctggg tgtggtggcc cctttgggct acaatggact    2520
cctcatcatg agctgtacct actatgcctt caagacccgc aacgtgcccg ccaacttcaa    2580
cgaggccaaa tatatcgcgt tcaccatgta caccacctgt atcatctggc tagcttttgt    2640
gcccatttac tttgggagca actacaagat catcacaact tgctttgcag tgagtctcag    2700
tgtaacagtg gctctggggt gcatgttcac tcccaagatg tacatcatta ttgccaagcc    2760
tgagaggaat gtccgcagtg ccttcaccac ctctgatgtt gtccgcatgc atgttggcga    2820
tggcaagctg ccctgccgct ccaacacttt cctcaacatc ttccgaagaa agaaggcagg    2880
ggcagggaat gccaattcta atggcaagtc tgtgtcatgg tctgaaccag gtggaggaca    2940
ggtgcccaag ggacagcata tgtggcaccg cctctctgtg cacgtgaaga ccaatgagac    3000
ggcctgcaac caaacagccg tcatcaaacc cctcactaaa agttaccaag gctctggcaa    3060
gagcctgacc ttttcagata ccagcaccaa gaccctttac aacgtagagg aggaggagga    3120
tgcccagccg attcgcttta gcccgcctgg tagcccttcc atggtggtgc acaggcgcgt    3180
gccaagcgcg gcgaccactc cgcctctgcc gccccacctg accgcagagg gaccccccct    3240
cttcctggcc gaaccagccc tcccaagggc cttgcccct cctctccagc agcagcagca    3300
accccctcca cagcagaaat cgctgatgga ccagctccag ggagtggtca gcaacttcag    3360
taccgcgatc ccggatttt cacgcggtgct ggcaggcccc gggggtcccg ggaacgggct    3420
gcggtccctg tacccgcccc cgccaccgcc gcagcacctg cagatgctgc cgctgcagct    3480
gagcaccttt ggggaggagc tggtctcccc gcccgcggac gacgacgacg acagcgagag    3540
gtttaagctc ctccaggagt acgtgtatga gcacgagcgg aagggaaca cggaagaaga    3600
cgaactggaa gaggaggagg aggacctgca ggcggccagc aaactgaccc cggatgattc    3660
gcctgcgctg acgcctccgt cgcctttccg cgactcggtg gcctcgggca gctcggtgcc    3720
cagctcccca gtgtccgagt cggtgctctg caccccctcc aacgtatcct acgcctctgt    3780
cattctgcgg gactacaagc aaagctcttc caccctgtaa gggggaaggg tccacataga    3840
aaagcaagac aagccagaga tctcccacac ctccagagat gtgcaaacag ctgggaggaa    3900
aagcctggga gtgggggcc tcgtcgggag gacaggagac cgctgctgct gctgccgcta    3960
ctgctgctgc tgccttaagt aggaagagag ggaaggacac caagcaaaaa atgttcaggc    4020
caggattcgg attcttgaat tactcgaagc cttctctggg aagaaaggga attctgacaa    4080
```

-continued

```
agcacaattc catatggtat gtaactttta tcacaaatca aatagtgaca tcacaaacat   4140
aatgtcctct tttgcacaat tgtgcataga tatatatatg cccacacaca ctgggccatg   4200
cttggcaagg aacagaccac gtggcatcca gtcggatcat gagttcacct gatgcattcg   4260
gagtgagctg gtggagccag acagagcagg tgcggggaag ggaagggcca ggccagaccc   4320
atcccaaacg gatgatggga tgatgggaca gcagttcctt gctcagaagc ccttctcccc   4380
gctgggctga cagactcctc atcttcagga gactcaggaa tggagcggta cagggctctc   4440
tcttcatcca ccgcaaccca tccagtgcca gctttgagat tgcacttgaa gaaaggtgca   4500
tggaccccct gctgctctgc agattccctt tatttaggaa aacaggaata agagcaaaat   4560
tatcaccaaa aagtgcttca tcaggcgtgc tacaggagga aggagctaga aatagaacaa   4620
tccatcagca tgagactttg aaaaaaaaaa cacatgatca gcttctcatg ttccatattc   4680
acttattggc gatttgggga aaaggccgga acaagagatt gttacgagag tggcagaaac   4740
ccttttgtag attgacttgt gtttgtgcca agcgggcttt ccattgacct tcagttaaag   4800
aacaaaccat gtgacaaaat tgttaccttc cacttactgt agcaaataat acctacaagt   4860
tgaacttcta agatgcgtat atgtacaatt tggtgccatt atttctccta cgtattagag   4920
aaacaaatcc atctttgaat ctaatggtgt actcatagca actattactg gtttaaatga   4980
caaataattc tatcctattg tcactgaagt ccttgtaact agcgagtgaa tgtgttcctg   5040
tgtccttgta tatgtgcgat cgtaaaattt gtgcaatgta atgtcaaatt gacctgtcaa   5100
tgtcaaccta gtagtcaatc taactgcaat tagaaattgt cttttgaata tactatatat   5160
atttttatg ttccaataat gttttataca tcattgtcat caatatctac agaagctctt   5220
tgacggtttg aatactatgg ctcaaggttt tcatatgcag ctcggatgga catttttctt   5280
ctaagatgga acttattttt cagatatttt ctgatgtgga gatatgttat taatgaagtg   5340
gtttgaaaat ttgttatatt aaagtgcac aaaaactgag agtgaaaata aaaggtacat    5400
tttataagct tgcacacatt attaacacat aagattgaac aaagcattta gattattcca   5460
ggttatatca ttttttttaaa gattttccac agctacttga gtgtctaaca tacagtaaca  5520
tctaactcag ctaataattt gtaaaatctt tatcaatcac attgtggcct cttttaattt   5580
ttatgttcat ggactttat tcctgtgtct tggctgtcat aacttttat ttctgctatt     5640
tgctgttgtg taatatccat ggacatgtaa tccacttact ccatctttac aatcccttt    5700
taccaccaat aaaaggattt tttcttgctg ttttgatttc ttctattatt tgtggaatga   5760
attataccc ccttaaatat ctttgtttat gccttatgtt cagtcatatt ttaatatgct    5820
tccttcatat tgaagctgct gatttctcag ccaaaaatca tcttagaatc tttaaatatc   5880
cattgcatca tttgttcaga atttaacatc cattccaatg ttggaggctt gtattactta   5940
tatttcatca tattctattg ccaagtttag tcagttccac accaagaatg aactgcattt   6000
cctttaaaaa ttattttaaa acacctttat tgaaagatc tcatgactga gatgtggact    6060
ttggttccat gttttcattg taagaaagca gagagcggaa aatcaatggc tccagtgatt   6120
aatagatggg tttttagtaa ttgacaaatt catgagggaa agcatatgat ctctttatta   6180
gtgaatcatg cttattttt actcttaacg ccactaatat acatccctaa tatcacaggg    6240
cttgtgcatt cagattttta aaaattagg atagataagg aaacaactta tattcaagtg    6300
taagatgata tcaggttggt ctaagacttt tggtgaacac gttcattcaa ctgtgatcac   6360
tttattactc tgaatgccta ctattatcct gattatgggg tctcctgaat aaatagagta   6420
ttagtctttta tgtcatcatt gttcaaaatt ggagatgtac acatacatac cctataccaa  6480
```

```
gagggccgaa actcttcacc ttgatgtatg ttctgataca agttgttcag cttcttgtaa    6540
atgtgttttc cttcggcttg ttactgcctt ttgtcaaata atcttgacaa tgctgtataa    6600
taaatatttt ctatttatt                                                 6619
```

```
<210> SEQ ID NO 3
<211> LENGTH: 65
<212> TYPE: DNA
<213> ORGANISM: Artificial Sequence
<220> FEATURE:
<223> OTHER INFORMATION: Synthetic oligonucleotide

<400> SEQUENCE: 3
gatcccgtgg acggagatgt catcatttca agagaatgat gacatctccg tccattttt    60 ggaaa                                                               65

<210> SEQ ID NO 4
<211> LENGTH: 64
<212> TYPE: DNA
<213> ORGANISM: Artificial Sequence
<220> FEATURE:
<223> OTHER INFORMATION: Synthetic oligonucleotide

<400> SEQUENCE: 4
gcttttccaa aaatggacg gagatgtcat cattctcttg aaatgatgac atctccgtcc    60
acgg                                                                64

<210> SEQ ID NO 5
<211> LENGTH: 439
<212> TYPE: PRT
<213> ORGANISM: Mus musculus

<400> SEQUENCE: 5
```

| | | | | | | | | | | | | | | |
|---|---|---|---|---|---|---|---|---|---|---|---|---|---|---|
| Met | Phe | His | Thr | Leu | Asp | Lys | Ile | Asn | Ala | Asp | Pro | Val | Leu | Pro |
| 1 | | | | 5 | | | | | 10 | | | | | 15 |

| Asn | Ile | Thr | Leu | Gly | Ser | Glu | Ile | Arg | Asp | Ser | Cys | Trp | His | Ser | Ser |
|---|---|---|---|---|---|---|---|---|---|---|---|---|---|---|---|
| | | | 20 | | | | | 25 | | | | | 30 | | |

| Val | Ala | Leu | Glu | Gln | Ser | Ile | Glu | Phe | Ile | Arg | Asp | Ser | Leu | Ile | Ser |
|---|---|---|---|---|---|---|---|---|---|---|---|---|---|---|---|
| | | 35 | | | | | 40 | | | | | 45 | | | |

| Ile | Arg | Asp | Glu | Lys | Asp | Gly | Leu | Asn | Arg | Cys | Leu | Pro | Asp | Gly | Gln |
|---|---|---|---|---|---|---|---|---|---|---|---|---|---|---|---|
| | 50 | | | | | 55 | | | | | 60 | | | | |

| Thr | Leu | Pro | Pro | Gly | Arg | Thr | Lys | Lys | Pro | Ile | Ala | Gly | Val | Ile | Gly |
|---|---|---|---|---|---|---|---|---|---|---|---|---|---|---|---|
| 65 | | | | | 70 | | | | | 75 | | | | | 80 |

| Pro | Gly | Ser | Ser | Ser | Val | Ala | Ile | Gln | Val | Gln | Asn | Leu | Leu | Gln | Leu |
|---|---|---|---|---|---|---|---|---|---|---|---|---|---|---|---|
| | | | | 85 | | | | | 90 | | | | | 95 | |

| Phe | Asp | Ile | Pro | Gln | Ile | Ala | Tyr | Ser | Ala | Thr | Ser | Ile | Asp | Leu | Ser |
|---|---|---|---|---|---|---|---|---|---|---|---|---|---|---|---|
| | | | 100 | | | | | 105 | | | | | 110 | | |

| Asp | Lys | Thr | Leu | Tyr | Lys | Tyr | Phe | Leu | Arg | Val | Val | Pro | Ser | Asp | Thr |
|---|---|---|---|---|---|---|---|---|---|---|---|---|---|---|---|
| | | | 115 | | | | | 120 | | | | | 125 | | |

| Leu | Gln | Ala | Arg | Ala | Met | Leu | Asp | Ile | Val | Lys | Arg | Tyr | Asn | Trp | Thr |
|---|---|---|---|---|---|---|---|---|---|---|---|---|---|---|---|
| | 130 | | | | | 135 | | | | | 140 | | | | |

| Tyr | Val | Ser | Ala | Val | His | Thr | Glu | Gly | Asn | Tyr | Gly | Glu | Ser | Gly | Met |
|---|---|---|---|---|---|---|---|---|---|---|---|---|---|---|---|
| 145 | | | | | 150 | | | | | 155 | | | | | 160 |

| Asp | Ala | Phe | Lys | Glu | Leu | Ala | Ala | Gln | Glu | Gly | Leu | Cys | Ile | Ala | His |
|---|---|---|---|---|---|---|---|---|---|---|---|---|---|---|---|
| | | | | 165 | | | | | 170 | | | | | 175 | |

| Ser | Asp | Lys | Ile | Tyr | Ser | Asn | Ala | Gly | Glu | Lys | Ser | Phe | Asp | Arg | Leu |
|---|---|---|---|---|---|---|---|---|---|---|---|---|---|---|---|
| | | | 180 | | | | | 185 | | | | | 190 | | |

-continued

```
Leu Arg Lys Leu Arg Glu Arg Leu Pro Lys Ala Arg Val Val Cys
        195                 200                 205
Phe Cys Glu Gly Met Thr Val Arg Gly Leu Leu Ser Ala Met Arg Arg
    210                 215                 220
Leu Gly Val Val Gly Glu Phe Ser Leu Ile Gly Ser Asp Gly Trp Ala
225                 230                 235                 240
Asp Arg Asp Glu Val Ile Glu Gly Tyr Glu Val Glu Ala Asn Gly Gly
                245                 250                 255
Ile Thr Ile Lys Leu Gln Ser Pro Glu Val Arg Ser Phe Asp Asp Tyr
            260                 265                 270
Phe Leu Lys Leu Arg Leu Asp Thr Asn Thr Arg Asn Pro Trp Phe Pro
        275                 280                 285
Glu Phe Trp Gln His Arg Phe Gln Cys Arg Leu Pro Gly His Leu Leu
    290                 295                 300
Glu Asn Pro Asn Phe Lys Lys Val Cys Thr Gly Asn Glu Ser Leu Glu
305                 310                 315                 320
Glu Asn Tyr Val Gln Asp Ser Lys Met Gly Phe Val Ile Asn Ala Ile
                325                 330                 335
Tyr Ala Met Ala His Gly Leu Gln Asn Met His His Ala Leu Cys Pro
            340                 345                 350
Gly Tyr Val Gly Leu Cys Asp Ala Met Lys Pro Ile Asp Gly Arg Lys
        355                 360                 365
Leu Leu Asp Phe Leu Ile Lys Ser Ser Phe Val Gly Val Ser Gly Glu
    370                 375                 380
Glu Val Trp Phe Asp Glu Lys Gly Asp Ala Pro Gly Arg Tyr Asp Ile
385                 390                 395                 400
Met Asn Leu Gln Tyr Thr Glu Ala Asn Arg Tyr Asp Tyr Val His Val
                405                 410                 415
Gly Thr Trp His Glu Gly Val Leu Asn Ile Asp Asp Tyr Lys Ile Gln
            420                 425                 430
Met Asn Lys Ser Gly Met Val
        435

<210> SEQ ID NO 6
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 6
ctttctccct tccttactgg                                             20

<210> SEQ ID NO 7
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 7
tggcttcatt cttggtgctt                                             20

<210> SEQ ID NO 8
<211> LENGTH: 23
<212> TYPE: DNA
<213> ORGANISM: Artificial Sequence
<220> FEATURE:
<223> OTHER INFORMATION: Synthetic oligonucleotide primer
```

<400> SEQUENCE: 8
acattattag gaccaggacg ccc  23

<210> SEQ ID NO 9
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 9
gaaactggca gatcgatggc atagc  25

<210> SEQ ID NO 10
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 10
ggagagcgga atggacgctt  20

<210> SEQ ID NO 11
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 11
accactggtg tgtcccggta  20

<210> SEQ ID NO 12
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 12
ccgagagcgg cttcccaag  19

<210> SEQ ID NO 13
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 13
agcttcctgc cgtcaatggg  20

<210> SEQ ID NO 14
<211> LENGTH: 3686
<212> TYPE: DNA
<213> ORGANISM: Mus musculus

<400> SEQUENCE: 14
gatctctact aactgagcta caccccctagc ccctctttgt ggtttaaatg agatgacagc  60
gggtaaagaa gcaagcctag gtcagtacct ggcatagagt agaagattaa gaaacctaca  120
tttccacagg gctgagaaga tggttcagtg gttaagatca cgtgctgttc ttgcagagga  180

```
cctaggttcc attctcaata tcaagatggt gactcccaac ttcctgtaac tcctgtctca    240
ggtcatttga tgctttcttc tggtctctga aagcagtgc ctatacattc acctagactc     300
acacacatat acataaaaaa atcataaaga ggaatgtttt cttcttttcc ttattttgaa    360
gtatcacaat gaattcctga gagacgatga atgtagtaac acagcttatt gcgaagattg    420
ggaccttggg gtcagggaga tacagtcctt ccaatgccct gctatccgag gtcccaggct    480
ccctctcctc tcctgtaaca ttgggataat aaccagcgac ttgataggac taagaggaaa    540
acaagccgtg cactgtgatt ggaaggtgtc ctggttgagg acaccaaagt gaatggcaaa    600
ggacggcttc tctcagcagg tgacactcca gtgacaggaa gccaggaggg gatatttcag    660
gcagaagaaa cagcagtaca atggctgaga gttcccatga ctagatctgt ctgggtagca    720
gtgaccatag tactctgccc aacaaagaca gacagaaaga caggcagcag aagttctgac    780
atgaccttct agtccagctc ctcccaaact ctatggcaca gaagttttga aaaacagttt    840
taaggccaac gtgagatcta aatgtgcatg gtgtcagtgc gaataaccct ccaggctggc    900
acctgaccga tcatgtgcaa gagtgtatgt caatggccaa gcttctaaat gctatatccc    960
agtttctgtc tttactgtat ccatcctaat gtaggtcaga agcacacagg ctgggatctg    1020
ctgaccaccc tgggtagcac atggaacaac gtttgtcatc actctaagtg cttcagaaat    1080
cattgccggg aaagggagaa agagaaacca aagattcaag gaccatggtg gtgttttgtc    1140
cttagagcag aggtcaatgt gacaagacas caaaattctg ctctgaaggg tctaagccct    1200
tctgggagga agttggctat gagtctgaga ctcgcaggtg agagccggcc cagggaagga    1260
atcctggggt gaggtgagaa cttttcgcgta aagcctcaga tgacctgggt tgcatggcag    1320
gtgctacaac gaaaaggaaa tgggtcattc tgatgtgaga aatgtccctc aatttcaggt    1380
ccctagaaat ctgatgatgg catcttccaa acttcactgc tgctcagaaa agcaggcttc    1440
acaatggcga cgtgaagtgg aagtcagcaa acagacagaa tgaatgggtc cccaaagcct    1500
ctaagtcttt acaactgtta ggtattatga tcctagcata gtcaagccta agaaaggaat    1560
gcacctggtc ccttagccga cgacggcaag catcgtctac agctctacct cattctcata    1620
ccgtggcttg caactctggc tgtgcagtag aacctggaag agagtttaga aaacactgat    1680
gtgaggctgg ggagatggct cagtcagtaa catgcttgta agtgtgggga cctgacttca    1740
cccccccagt gcccacataa gaagccagga atggtggtag acccctgtag tccctgtgcc    1800
ggagaggcga aatccctgga gctttctggt cagccactac ccaaaggttc agtgggagac    1860
cctgtcgcaa aaaacaaagt ggaaagtgag taggcaaacc atttatgttg gtctttgtca    1920
tccacctgca catgcatata caaacatgtg ggcatgcatg ccttccacag cacatatact    1980
gtaaatgcac acatctgcat gcctgcatgc acacatgcac acacacttac atcgctgatg    2040
ccttgaacat atcattaaca gtcccattca atgtccagaa cccagaaata caaactgata    2100
ttgggttagt cacaccttaa taccacaggg gtggcacaga ggacatgtgt agggacacct    2160
gtgtattttc ctttcttcct tctccttttc tttcttttta agatgggggtc tctctacgta    2220 gccatggcta tcctgagact cacgatgtag actgggctgg cttccaactc acatagatca    2280
ccctgcctct gctttctgaa tgttgggatt aaagtcatgg gtcttttagca gacaggcaca    2340 cacacctggc tgctgtgtac gtttctcaac cttaagaatt cctttgaaac taacaaggca    2400
cttgacattc acgttcaagg cactcttaga ctccaactgg aacaattcta agtcggcaat    2460
ttgtatagat ctcatgacac cacgacagtc ctgttcgcac caggaaggga ctaatgctct    2520
ggcaaatggc cgccacggtc catctgcaca gcccgtggta cctagaggaa gcacataggg    2580
```

-continued

```
gtacaccttc ctaaattaaa gcttgattat gccaaacctc aatgcaatcg aaagatttcc      2640
ttgcaagtcc cactccagtt tgtccaattg cagagaaatg acaactgtga ataattggta      2700
gcatacggtt ccacgcaaat taaatacaaa tctgcttcat ggatgtgctg aacaagagaa      2760 gaggggggcta ttatttggaa gcaggaggat gcctaattgt gcacaaaaca gctccttgta    2820
cactggcttt aaataaacgt ttctttattg ggggggtgt gatctcctgt ggcggtctct       2880
ctcccatgtc agccagcagt catggggag aagtacttag caatgcacag gtctataaag       2940
ggcctttgac ggaatgctcc ctctatctat tgacgcactg ggaagtctga ggtcacaagc     3000
ttggctggga cacatgagcc aataaagag gctgatttta ccctcctgac acaaagccag      3060
acactttatc agcttcattg tgcacttagg gtcatgtgct aacaaagagg atttctctgg    3120
ttataatccc cttaatgatg gcttctccca tccctccgcc ccccccccc gtgccccacc      3180 agggccccgt ggcttggcga gccagagaga ataaaggcaa cacggtgctt ggcttttgaa   3240
ctgagttcaa ggcaattaag gtcaagggct agggagagaa ggaggaggct tagaaacagc   3300
agcataataa gcagtatggc tggagcactc tgtaaattaa ctcaattaga cagagcctga    3360
tttaacaagg aagactggcg agaagctccc ctcattaaac ctgatgttag aggagcttcg   3420
gatgaaatta aatcagtgtt agttgtttga gtcacataaa attgcatgag cgtgtacaca   3480
tgtgcacacg tgtaggctct gtgatttagg tgggaattt gagaggagag gaaagggcta    3540
gaactaaacc caaagaaaag gaaagaagag aagaggaaag gaaagaaaaa agaaaaggca  3600
atttgagtga gtaaaggttc cagaactcag gagtggaaga caaggagtaa agtcagacag   3660
aaaccaggtg ggacgccggc caggcc                                         3686
```

<210> SEQ ID NO 15
<211> LENGTH: 624
<212> TYPE: DNA
<213> ORGANISM: Homo sapiens

<400> SEQUENCE: 15

```
cccgggtggc atccctgtga cccctcccca gtgcctctcc tggccctgga agttgccact      60
ccagtgccca ccagccttgt cctaataaaa ttaagttgca tcattttgtc tgactaggtg     120
tccttctata atattatggg gtggagggg gtggtatgga gcaaggggca agttgggaag     180
acaacctgta gggcctgcgg ggtctattgg gaaccaagct ggagtgcagt ggcacaatct    240
tggctcactg caatctccgc ctcctgggtt caagcgattc tcctgcctca gcctcccgag    300
ttgttgggat tccaggcatg catgaccagg ctcagctaat ttttgttttt ttggtagaga    360
cggggtttca ccatattggc caggctggtc tccaactcct aatctcaggt gatctaccca    420
ccttggcctc ccaaattgct gggattacag gcgtgaacca ctgctccctt ccctgtcctt    480
ctgattttaa aataactata ccagcaggag gacgtccaga cacagcatag gctacctggc    540
catgcccaac cggtgggaca tttgagttgc ttgcttggca ctgtcctctc atgcgttggg    600
tccactcagt agatgcctgt tgaa                                          624
```

ANIMAL MODEL, CELLS, AND TREATMENT FOR MALIGNANT MELANOMA

This application claims the benefit of priority from U.S. provisional application Ser. Nos. 60/649,022, filed Feb. 1, 2005 and 60/563,131, filed Apr. 16, 2004, whose contents are incorporated herein by reference in their entireties.

This invention was made in the course of research sponsored by the National Institutes of Health (Grant Nos. RO1CA074077, RO1CA108720 and F31CA103364). The U.S. government may have certain rights in this invention.

BACKGROUND OF THE INVENTION

Melanoma incidence and mortality rate in European populations are increasing worldwide. Approximately 10% of melanomas occur in individuals with familial predisposition, but loci associated with susceptibility to multiple melanomas have yet to be identified. Spontaneous and induced mouse mutants are tools for uncovering new genes and pathways implicated in a particular disease. An insertional mutant, TG3, was generated by pronuclear injection with a 2-kb genomic fragment, clone B (Colon-Teicher, et al. (1993) Nucl. Acids Res. 21:2223-2228). The previously described TG3 line is predisposed to develop multiple melanomas primarily affecting the pinnae of the ear, perianal region, eyelid, snout, trunk and legs (Chen, et al. (1996) J. Invest. Dermatol. 106:1145-1150; Zhu, et al. (1998) J. Invest. Dermatol. 110:247-252). Metastases to distant organs are detected in some cases (Chen, et al. (1996) supra; Zhu, et al. (1998) supra). Melanoma susceptibility was found to be linked with the presence of the transgene.

Glutamate is the predominant excitatory neurotransmitter in the mammalian central nervous system, and it can signal through a variety of glutamate receptors. Although once thought to be restricted to the central nervous system, glutamate signaling has been shown in a variety of non-neuronal tissues, including bone and skin (Skerry and Genever (2001) Trends Pharmacol. Sci. 22:174-181). There are two main categories of glutamate receptors. The ionotropic receptors are glutamate-gated, cation-specific ion channels, whereas the metabotropic receptors are coupled to intracellular signal-transduction pathways through G proteins. Metabotropic glutamate receptors are members of the large family of seven-transmembrane-domain G protein-coupled receptors. Both Grm1 and Grm5 (also called Gprc1 and mgluR5) are group 1 metabotropic glutamate receptors coupling primarily to phosphoinositide hydrolysis. Grm1 has also been shown to couple to multiple intracellular signaling cascades including adenylate cyclase activation (Hermans and Chaliss (2001) Biochem. J. 359:465-484). Mice carrying null mutations in Grm1 have severe deficits in motor coordination and spatial learning (Aiba, et al. (1994) Cell 79:377-388; Aiba, et al. (1994) Cell 79:365-375; Conquet, et al. (1994) Nature 372:237-243), but no melanocyte defect has been described. Metabotropic glutamate receptors have not previously been implicated in tumorigenesis; however, a variety of G protein-coupled receptors and G proteins, including those that signal through phosphoinositide hydrolysis and cAMP accumulation, have been implicated in tumorigenesis through either mutational activation or over-expression (Dhanasekaran, et al. (1995) Endocr. Rev. 16:259-2701; Gutkind (1998) Oncogene 17:1331-1342). In addition, glutamate has been linked to tumor growth in both neuronal and non-neuronal cancers (Takano, et al. (2001) Nat. Med. 7:1010-1015; Rzeski, et al. (2001) Proc. Natl. Acad. Sci. USA 98:6372-6377). Further, glutamate has been shown to stimulate proliferation of lung carcinoma cells in serum-deprived media, and antagonists to the ionotropic glutamate receptors, AMPA and NMDA receptors, have been shown to inhibit proliferation and increase cell death in a calcium-dependent manner in a variety of non-neuronal cancers (Rzeski, et al. (2001) supra). Agonist stimulation of Grm5 in subconfluent melanocyte culture has also been shown to result in melanocyte proliferation (Frati, et al. (2000) J. Cell. Physiol. 183:364-372).

U.S. Pat. No. 5,869,609 teaches the identification, isolation and purification of Grm1. This reference further discloses anti-Grm1 antibodies for use in identifying agonists and antagonists of Grm1-mediated neuronal excitation, as well as in methods of diagnosis and/or treatment of diseases such as, for example, cerebral ischemia, Parkinsons, senile dementia and other cognitive disorders, Huntington's chorea, amyotrophic lateral sclerosis, emesis, and migraine. This reference does not teach a role for Grm1 in the development of melanocytic neoplasms.

U.S. Pat. No. 6,084,084 discloses a human metabotropic glutamate receptor 8 (mGluR8) protein and an immunoassay in which an antibody to mGluR8 is used to identify the number and/or location and/or functional integrity of mGluR8 or the presence of a cancer, e.g., an ectopic tumor of the central nervous system or peripheral nervous system. This reference does not disclose how mGluR8 is altered in a tumor cell nor does it teach the unscheduled expression of a glutamate receptor in malignant melanoma.

SUMMARY OF THE INVENTION

A correlation has now been identified between the up-regulation of Grm1 and the onset of melanoma. As a result, the instant invention will allow for the development of effective treatments for melanoma by enabling the discovery of novel therapeutic agents that inhibit or antagonize the activities of the Grm1 receptor present in melanoma cells.

Accordingly, the present invention is a transgenic non-human animal whose genome contains a transgene composed of a nucleotide sequence encoding a metabotropic glutamate receptor 1 (Grm1) operably linked to a melanocyte-specific promoter, wherein the transgenic non-human animal expresses the Grm1 in melanocytes and displays a predisposition for the development of a melanoma.

A vector containing a nucleic acid sequence encoding a Grm1 operably linked to a melanocyte-specific promoter and a host cell containing and capable of expressing the same are further embodiments of the present invention.

A transgenic non-human animal or host cell of the invention is useful for identifying agents for the prevention or treatment of a melanoma. Accordingly, the present invention also relates to a screening method involving contacting a transgenic non-human animal or host cell of the invention with an agent and determining whether the agent inhibits or decreases at least one sign or symptom of the melanoma in the animal or cell. In one embodiment, the agent is an antagonistic antibody, protein or small organic molecule, wherein the organic molecule has a molecular weight of 200-1000.

The present invention also relates to a method for producing a melanoma cell line by isolating a cell from an amelanotic tumor and culturing the cell in the presence of a Grm1 agonist for a sufficient amount of time to establish cell growth and a melanoma cell line.

The present invention further relates to a method for diagnosing a melanoma. The method involves detecting the presence of RNA transcript encoding Grm1 or Grm1 protein, using an anti-Grm1 antibody, in a sample wherein the presence of Grm1 transcript or Grm1 protein in the sample is indicative of a melanoma. In particular embodiments, the antibody is a monoclonal or polyclonal antibody.

A kit for diagnosing a melanoma is also provided.

DETAILED DESCRIPTION OF THE INVENTION

A signaling pathway responsible for the development of melanocytic neoplasms has now been identified. Using a physical mapping approach, the transgene insertion site of the TG3 mouse mutant was mapped to chromosome 10 in a region orthologous to human chromosome 6q23-24. Physical mapping identified multiple tandem insertions of the transgene into intron 3 of Grm1 (also called Gprc1a and mGluR1) and this integration event resulted in the deletion of 70 kb of intronic sequence. The physical map created spans a genomic region of roughly 1 Mb flanking the integration site. As the melanoma phenotype observed in the TG3 line may have been due to aberrant gene expression of either Grm1 or a flanking gene, the full-length sequence of Grm1 was determined and cDNA sequences of two flanking genes, Rab32 and Shprh, were cloned.

The tissue-specific expression of Grm1, Rab32, and Shprh was evaluated by northern blot analysis. In normal tissues, Grm1 expression was detected in brain, heart, and kidney but not in placenta, lung, liver, skeletal muscle, or pancreas. In contrast, Rab32 and Shprh were expressed, albeit at varying levels, in all tissues examined. It was also determined by RT-PCR and western blot analyses whether these three genes had aberrant expression in melanomas removed from TG3 mice. Grm1 expression was detected by both RT-PCR and western blot in pinnae tumors but not in mouse melanocyte cell line melan-a or in normal pinnae. To control for differing melanocyte number in normal and tumor pinnae, duplex RT-PCR was carried out with melanocyte-specific marker Tyrp1. When the level of Tyrp1 expression was comparable in normal and tumor pinnae, Grm1 expression was detected only in tumor pinnae and brain. Western blot analysis confirmed the ectopic expression of Grm1 in melanoma tumors from the TG3 line and its absence in normal pinnae from C57BL/6J mice.

To show that overexpression of Grm1 in melanocytes leads to melanocytic hyperplasia and melanoma, a new transgenic line was created in which expression of Grm1 was targeted to the melanocytes by the dopachrome tautomerase (Dct) promoter (Budd and Jackson (1995) *Genomics* 29:35-43). This promoter sequence has been used to drive expression of lacZ specifically in melanoblasts and melanocytes (Mackenzie, et al. (1997) *Dev. Biol.* 192:99-107). After transient transfection of this Dct-Grm1 construct into both NIH3T3 and melan-a cells, expression of Grm1 was observed exclusively in the melanocyte cell line. In contrast, a CMV-driven construct permitted the expression of Grm1 in both NIH3T3 and melan-a cells.

After pronuclear injection of the Dct-Grm1 transgene, three transmitting founders were obtained from 53 live offspring. One founder, Tg(Grm1)EPv (E), developed pigmented lesions on the pinnae and tail at 5-6 months of age, which progressed into raised lesions by 6-7 months. Tumor burden required removal of the tail from this mouse at 14 months, and the mouse was killed at 20 months of age. To assess transgene expression, whole-mount in situ hybridization on 12.5-day-old embryos from all three founder lines was performed. Only transgenic embryos derived from the E line had strong expression of Grm1 in a ubiquitous ectodermal distribution. Therefore, it is possible that expression of Grm1 may influence the growth of melanocytes through the release of growth factors or changes in cell adhesion by adjacent keratinocytes. To confirm that the absence of tumors in the other two lines, Tg(Grm1)APv (A) and Tg(Grm1)CPv (C), was due to lack of Grm1 expression, western blot analysis was carried out in pinnae from 6-8-week old mice from all three lines. Expression of Grm1 was observed only in pinnae removed from mice derived from the E line.

All 107 transgenic offspring derived from the E line presented initially with flat hyperpigmented lesions that subsequently developed into raised overt melanomas. These lesions always affected the pinnae and tail, albeit with different severity. Over five generations of mice, tumor onset had 100% penetrance. Flat, pigmented lesions were also observed on the limbs and around the snout and, occasionally, raised tumors on the eyelid were seen. Detailed histopathological analysis of mice from the E line showed hyperproliferation of the dermal melanocytes in the pinnae and tail. The submandibular and inguinal lymph nodes, but not distant lymph nodes, were pigmented and enlarged. The presence of melanoma cells were confirmed in the submandibular and inguinal lymph nodes by verifying expression of Tyrp1. In contrast to TG3, gross pigmented lesions were not observed in distant organs of E mice after morphologic evaluation. Further, no melanoma cells were observed in a variety of distant organs including the lung, liver, kidney and spleen after histopathological analysis, even in aged mice killed because of primary tumor burden.

The predisposition toward tumor formation on the hairless skin areas rather than the trunk reflects the retention of dermal melanocytes in these areas compared with the postnatal reduction of dermal melanocytes in haired skins (Reedy, et al. In: The Pigmentary System: Physiology and Pathophysiology, eds. Nordlund, et al., Oxford University Press, New York, 1998). In contrast to the original TG3 insertional mutant line, the E line showed a predisposition toward tumors affecting the tail, an absence of tumors affecting the perianal region and harderian gland and an absence of metastases in distant organs. The phenotypic differences between these lines could be due to differences in the regulation of Grm1 expression between these two lines or to the presence of the clone B transgene in TG3 mice influencing the expression of other genes. The otherwise similar clinical and histopathological phenotype indicates that the susceptibility to melanoma of the original insertional mutant was due to the dysregulation of Grm1 expression.

Expression of GRM1 in human melanomas was also examined herein. Duplex RT-PCR analysis indicated that GRM1 was not expressed in two benign nevi but was expressed in 7 of 19 melanoma samples. Western-blot analysis likewise showed that GRM1 was expressed in 12 of 18 melanoma cell lines but not in the normal human melanocytes.

Further analysis of the presence of GRM1 in human samples is summarized in Table 1.

TABLE 1

| Source of Sample | Samples expressing Grm1/Total number of Samples |
|---|---|
| Normal | |
| Mole | 0/2 |
| Skin | 0/2 |
| Tumor | |
| Primary | 5/7 |
| Nodal | 1/3 |
| Recurrent Primary | 1/1 |

TABLE 1-continued

| Source of Sample | Samples expressing Grm1/Total number of Samples |
|---|---|
| Metastasis | |
| Nodal | 5/8 |
| In-Transit | 4/10 |
| Distant | 3/6 |

Attempts to establish tumor cell lines from tumors on TG3 mice were unsuccessful as the excess melanin appeared to be toxic for cell growth under culture conditions. In an effort to generate a transformed melanocytes cell line, the TG-3 mouse line was mated with an albino strain of mouse (Cohen-Salal, et al. (2001) Pigment Cell Res. 14:466-474). Using both RT-PCR and western blot analysis, it was shown that Grm1 was also involved in the spontaneous development of cutaneous amelanotic melanoma in the albino transgenic progeny which were tyrosinase and melanin deficient. Further, immunohistochemical staining for Grm1 or Tyrp1 on ear samples from control and amelanotic tumor transgenic mice was conducted. For control tissue sections, modest labeling of Grm1 and Tyrp-1 was shown in the epithelial layer and dermis, respectively. Sections of ear tumor from amelanotic transgenic mice showed strong staining for Grm1. The dermis contained an abundance of heavily labeled tumor cells. At high magnification, the label was distinct. Ear tumor stained for Tyrp-1 showed discrete and punctuate labeling, presumably demonstrating premelanosomes in the amelanotic melanocytes.

To further analyze the signaling events mediated by Grm1 in transformed melanocytes, cell lines derived from ear tumor bearing albino mice (Cohen-Salal, et al. (2001) supra) were generated. Tumors from these mice were sectioned in two halves. Protein extraction was performed on one part of the tumors and western immunoblots were done to verify the ectopic expression of Grm1. The other half of the tumor was used to generate homogeneous in vitro melanoma cell lines by gentle selection of melanocyte cells over keratinocytes and fibroblasts through differential geneticin resistance. Initial efforts to directly establish cell lines on standard culture medium supplemented with geneticin were unsuccessful. Unexpectedly, the addition of Grm1 agonist, L-quisqualate, to the culture medium enabled the establishment of melanoma cell lines. Based on morphology and growth rate, $10^{-5}$ M quisqualate was sufficient to establish growth in culture. It was found that the agonist could be removed after about eight weeks of growth and the cells remained viable and growth competent in the absence of the agonist. Ten cells lines namely LL1A, LL1T, Nu1, Nu2, MMB3A, MMB3T, 4045A, 4045T, 4046T, 4046A, were successfully generated from at least six independent mice tumors. Given that these mouse melanoma cell lines behave very similarly in culture, data presented herein is of representative cell lines. Ectopic expression of Grm1 was observed in these cell lines as determined by immunofluorescent staining whereas normal melanocyte cultures (Melan-a) lacked Grm1 expression. Cytoplasmic staining for Grm1 has also been reported in other cellular systems (Tadokoro, et al. (1999) Proc. Natl. Acad. Sci. USA 96:13801-13806). To verify the melanocytic origin of these cells, co-staining of the cells was performed with Tyrp-1. Grm1 and Tyrp-1 were found to co-localize in these tumor cell lines.

Normal mouse melanocytes require the phorbol ester 12-o-tetradecanoyl phorbol-13-acetate (TPA) in order to grow in vitro, and the loss of this requirement is one of the hallmarks of transformed melanocytes (Dotto, et al. (1989) J. Cell Biol. 109:3115-3128). Thus, the isolated tumor cell lines were analyzed to determine whether TPA was required for cell proliferation. Tumor cell growth was found to be independent of TPA, whereas normal melanocyte cell line Melan-a required TPA for proliferation. In addition, tumor cell lines readily formed colonies in soft-agar, and subcutaneous injection of tumor cells in nude mice formed tumors, whereas normal melanocytes did not. These data indicate that these cell lines retain their transformed phenotype in vitro.

It is well-established in neuronal systems, as well as in Grm1-transfected cells, that the activation of Grm1 by agonists leads to the activation of phospholipase C and further hydrolysis of phosphoinositol bisphosphate (PIP2) to inositol triphosphate (IP3) and diacylglycerol (DAG) (Joly, et al. (1995) J. Neurosci. 15(5 Pt 2):3970-81; Hermans, et al. (2001) Biochem. J. 359(Pt 3):465-84). Accordingly, it was determined whether the ectopic expression of Grm1 observed in melanoma cells would also lead to similar signaling events as those described in other systems. Tumor cells stimulated with quisqualate, a Group I metabotropic glutamate receptor-specific agonist, for 5 minutes resulted in enhanced IP3 accumulation by 2.2- to 4.2-fold. Pre-incubation of tumor cells with LY368675 (LY), a Grm1-specific antagonist, prior to incubation with agonist inhibited IP3 accumulation. To further investigate the specificity of IP3 induction by Grm1 agonist, cells were transiently transfected with dominant-negative constructs of Grm1 (Francesconi and Duvoisin (1998) J. Biol. Chem. 273(10): 5615-24). Expression of the dominant-negative forms of the receptor was confirmed by western blot analysis. Cells transfected with the dominant-negative Grm1 were unable to induce IP3 accumulation in tumor cells upon agonist treatment, whereas vector-transfected cells were unaffected. These results demonstrate that expression of these dominant-negative forms of Grm1 result in a loss of function of the receptor as shown by reduced IP3 accumulation.

BRAF has been shown to be a mediator of GPCR signaling in melanocytes leading to extracellular-regulated kinase (ERK) activation (Busca, et al. (2000) EMBO J. 19(12):2900-10). Furthermore, frequent activating mutations of BRAF have been reported in human malignant melanoma, short-term melanoma cultures (Davies, et al. (2002) Nature 417(6892):949-54), and human melanoma cell lines (Satyamoorthy, et al. (2003) Cancer Res. 63(4): 756-9). A high proportion of the same lines showed constitutive ERK activation, suggesting that activating mutations of BRAF kinase were responsible for the constitutive ERK activation in these lines (Satyamoorthy, et al. (2003) supra). Therefore, it was determined whether BRAF is also mutated in the mouse melanoma cell lines. RNA was isolated from several ear tumors and from all tumor-derived cell lines. RT-PCR was conducted using primers flanking the most common human BRAF mutation. None of the mouse melanoma lines or tumor samples contained the BRAF mutation in the corresponding human BRAF position (Val600Glu).

To examine whether ERK1/2 were activated after Grm1 activation, cells were treated for the indicated times with the agonist Quisqualate. After treatment, melanoma cells were lysed and the activation of ERK1/2 was determined using antibodies against the phosphorylated forms of ERK1/2. An increase in the phosphorylation of ERK1/2 was observed after 5 minutes of tumor cell stimulation with quisqualate ($10^{-5}$ M). After 15 minutes, this phosphorylation was reduced to background levels. An anti-ERK1/2 antibody recognizing all ERK proteins indicated that the increase in ERK1/2 phosphorylation did not reflect an increase in total ERK protein. Similar experiments with other cell lines showed very similar time-dependent pattern of ERK activation.

To demonstrate that the activation of ERK1/2 was specifically mediated by Grm1 activation, melanoma lines were pretreated (30 minutes) with the antagonist LY367385 before agonist challenge. Activation of ERK1/2 by quisqualate was abrogated in the presence of this antagonist.

To confirm the specificity of ERK activation by Grm1, dominant-negative mutants of Grm1 were employed. Melanoma cells lines were transiently transfected with dominant-negative mutants of Grm1 and expression of the Grm1 mutants was analyzed by western blot analysis. ERK activation by Grm1 agonist was inhibited in melanoma cells transfected with mutant Grm1, whereas vector transfected cells remained unaffected. Likewise, siRNA, specific for Grm1 nucleic acid (i.e., SEQ ID NO:3 and SEQ ID NO:4), inhibited ERK activation compared to cells transfected with an unrelated siRNA sequence. These results indicate that the activation of ERK1/2 is specifically mediated by Grm1 in melanoma cells.

Upon IP3 accumulation in cells, calcium is released from the endoplasmic reticulum to the cytoplasm, allowing these ions to act as second messengers that bind to calmodulin and further activate calcium-calmodulin-dependent kinases that are capable of activating mitogen-activated protein kinases (MAPKS) (Soderling (1999) *Trends Biochem. Sci.* 24(6): 232-6). Accordingly, it was determined whether IP3 accumulation in the tumor cell lines disclosed herein, upon Grm1 agonist treatment, would yield intracellular calcium signaling that could affect ERK activation. Depletion of intracellular calcium in these cells was obtained by chelating extracellular calcium with EGTA, which obligates calcium to exit the cell in order to maintain calcium homeostasis. EGTA treatment of the melanoma cells caused a time-dependent decrease in ERK activation by quisqualate. In addition, chelating intracellular calcium, by the preincubation of cells with BAPTA-AM for 30 minutes prior to agonist challenge, lead to a dose-dependent decrease in ERK activation in the presence of extracellular calcium. In contrast, when cells were treated in the same way but in calcium-free media, activation of ERK was completely abolished, indicating that intracellular calcium is essential for Grm1-mediated ERK1/2 activation.

PIP2 hydrolysis resulting from Grm1 activation leads to the production of IP3 and DAG. DAG can then activate protein kinase C (PKC). PKC has been demonstrated to stimulate ERK1/2 activation by activating the upstream kinase Raf (Marinissen and Gutkind (2001) *Trends Pharmacol. Sci.* 22(7):368-76). Thus, it was determined whether the activation of ERK1/2 by Grm1 is also mediated by PKC in the tumor cell lines disclosed herein. Melanoma cell lines were preincubated for 15 minutes with 10 μM of the PKC inhibitor staurosporine, before quisqualate treatment. Inhibition of PKC resulted in abrogation of ERK phosphorylation. These results indicate that PKC may be mediating ERK1/2 activation in the melanoma lines.

The PKC family of proteins are composed of several groups, and are classified into conventional isoforms: alpha, beta I, beta II, gamma; novel isoforms: delta, epsilon, eta, theta; and atypical isoforms: lambda, and zeta. Conventional isoforms contain domains that associate to phospholipids in a calcium-dependent fashion and also associate with DAG. Novel isoforms do not have a calcium-dependent phospholipid binding domain and do not require it for their activity, but can associate with DAG. To identify the specific isoform(s) of PKC involved in Grm1-mediated ERK activation, kinase-negative mutants of PKC alpha, beta II, delta, and epsilon were introduced into the tumor cell lines disclosed herein. Constructs encoded either wild-type PKC isoforms or single-base mutations in the ATP binding site of the PKC (i.e., kinase dead mutants (Oka, et al. (2002) *Biochem. Biophys. Res. Commun.* 294(5):1109-13). Tumor cells were co-infected with adenoviruses carrying a GFP control vector, and wild-type or mutant copies of PKC, at multiplicity of infection (MOI) of 5 and 25. Images of GFP were taken at different time points and optimal expression was observed 24 hours post-infection. Infected or non-infected control cells were then stimulated with quisqualate for 5 minutes and cell lysates were used for western blot analysis of phosphorylated ERK1/2, PKC, and ERK to show levels of equal loading. The isoforms with the highest level of endogenous expression were PKC alpha and PKC epsilon. PKC beta II and delta had lower levels of endogenous expression in the melanoma cells. In fact, similar differences in expression levels among the different PKC isoforms in B16 mouse melanoma cells has been observed (Szalay, et al. (2001) *J. Histochem. Cytochem.* 49(1):49-66). No significant changes in quisqualate-induced phospho-ERK were observed in wild-type or kinase-negative PKC alpha- or beta II-infected cells. For PKC delta, wild-type, as well as kinase-negative PKC, infection resulted in a significant decrease in the level of phopshorylated ERK, revealing the non-specific nature of this event, which may be due to general toxicity of the infection. Consistent inhibition of ERK activation was detected only in cells infected with kinase-negative PKC epsilon.

Using the mouse model disclosed herein, it has now been demonstrated that the glutamate receptor 1 (Grm1) signaling pathway is involved in the development of melanocytic neoplasms. While the present invention provides for the production of transgenic mouse models of melanoma, it is understood by those skilled in the art that the present invention, in general, provides non-human animal models of human melanoma. The transgenic non-human animals and cells lines of the present invention are advantageous over presently used model systems as tumor onset occurs without the use of a carcinogenic agent. The transgenic animals permit the analysis and elucidation of functional interactions between Grm1 signaling pathway components in a biologically relevant setting, and serve as a powerful model for evaluating the efficacy of mechanism-based therapeutic agents targeting this signaling pathway. The transgenic animals and cell lines of the present invention can also be used for the development of various treatments for melanoma including the identification of various therapeutically active agents including but not limited to other proteins, peptides, peptidomimetic drugs, small molecule drugs, chemicals and nucleic acid-based agents.

The term non-human animal is used herein to include all vertebrate animals, except humans. It also includes an individual animal in all stages of development, including embryonic and fetal stages. A transgenic animal is any animal containing one or more cells bearing genetic information altered or received, directly or indirectly, by deliberate genetic manipulation at a subcellular level, such as by targeted recombination or microinjection or infection with recombinant virus. The term transgenic animal is not intended to encompass classical cross-breeding or in vitro fertilization, but rather is meant to encompass animals in which one or more cells are altered by, or receive, a recombinant DNA molecule. This recombinant DNA molecule can be specifically targeted to a defined genetic locus, can be randomly integrated within a chromosome, or it can be extrachromosomally replicating DNA.

In particular embodiments of the present invention, a host cell or non-human animal is transformed to express Grm1 thereby predisposing said cell or animal to the development of a melanoma. The production of recombinant DNA, vectors, host cells, and proteins by genetic engineering techniques is well-known. See, e.g., U.S. Pat. No. 4,761,371; U.S. Pat. No. 4,877,729; U.S. Pat. No. 4,912,038; and U.S. Pat. No. 4,879,224 incorporated herein by reference and Sambrook and Russell (2001) In: Molecular Cloning, a Laboratory Manual, Cold Spring Harbor Laboratory; 3rd edition.

Nucleic acid sequences encoding Grm1 can be isolated using the polymerase chain reaction (PCR) procedure and splicing by overlap extension (SOE), as is known in the art (see U.S. Pat. No. 4,683,195 and U.S. Pat. No. 4,683,202) or by using conventional restriction enzyme-based cloning techniques. For PCR methods, primers can be designed by the skilled artisan based of the sequence provided as GENBANK accession number AF320126 (SEQ ID NO:1), NM_000838 (SEQ ID NO:2), HSU31215, HSU31216 or paralogs or orthologs thereof. Source DNA for PCR amplification or restriction enzyme digestion can be in the form of genomic DNA or cDNA.

Grm1 protein can be synthesized or expressed in host cells or transgenic animals transformed with a vector containing nucleic acid sequences encoding Grm1. A vector is a replicable nucleic acid construct. Vectors are used herein either to amplify nucleic acid sequences encoding Grm1 and/or to express nucleic acid sequence encoding Grm1. A Grm1 expression vector is a replicable nucleic acid construct in which a nucleic acid sequence encoding Grm1 is operably linked to a melanocyte-specific promoter and other suitable control sequences capable of effecting the expression of Grm1 in a melanocyte. A melanocyte-specific promoter is intended as a transcriptional regulatory sequence which limits expression of an operably linked transgene to melanocytes with little or no expression in any other cell type. Suitable melanocyte-specific promoters which can be used to drive expression of Grm1 in host cells and animals of the invention include, but are not limited, the Trp-1 promoter (Jackson, et al. (1991) *Nucleic Acids Res.* 19(14):3799-804), dopachrome tautomerase (Dct) promoter (Budd and Jackson (1995) supra), QNR-71 promoter (Turgue, et al. (1996) *EMBO J.* 15(13):3338-50), or promoters to orthologs or paralogs thereof. The need for other suitable control sequences will vary depending upon the host cell or animal selected and the transformation method chosen. Generally, other control sequences include a sequence encoding an enhancer, a sequence encoding suitable mRNA ribosomal binding sites, and sequences which control the termination of transcription and translation. Nucleic acids are said to be operably linked when they are functionally related to each other. For example, a promoter is operably linked to a coding sequence if it controls the transcription of the sequence and a ribosome binding site is operably linked to a coding sequence if it is positioned so as to permit translation. Generally, operably linked means contiguous and, in the case of leader sequences, contiguous and in frame.

Amplification vectors do not require expression control domains. All that is needed is the ability to replicate in a host, usually conferred by an origin of replication, and a selection gene to facilitate recognition of transformants.

Vectors useful for practicing the present invention include plasmids, viruses (including phage), retroviruses, and integratable DNA fragments (i.e., fragments integratable into the host genome by homologous recombination). The vector replicates and functions independently of the host genome, or may, in some instances, integrate into the genome itself. Suitable vectors contain replicon and control sequences which are derived from species compatible with the intended expression host. An origin of replication can be provided either by construction of the vector to include an exogenous origin, such as may be derived from SV40 or other viral source (e.g., Polyoma, Adenovirus, VSV, or BPV), or can be provided by the host cell chromosomal replication mechanism. If the vector is integrated into the host cell chromosome, the latter may be sufficient.

Rather than using vectors which contain viral origins of replication, one can transform mammalian cells by the method of co-transformation with a selectable marker and the Grm1 nucleic acid sequences. An example of a suitable selectable marker is dihydrofolate reductase (DHFR) or thymidine kinase. See U.S. Pat. No. 4,399,216. Such markers are proteins, generally enzymes, that enable the identification of transformant cells, i.e., cells which are competent to take up exogenous DNA. Generally, identification is by survival of transformants in culture medium that is toxic, or from which the cells cannot obtain critical nutrition without having taken up the marker protein.

Transformed host cells are cells which have been transformed or transfected with the Grm1 or Grm1 containing vectors using standard methods. Transformed host cells ordinarily express Grm1, but host cells transformed for purposes of cloning or amplifying nucleic acid sequences encoding Grm1 need not express the protein.

Suitable host cells generally include higher eukaryotic cells including established cell lines of mammalian origin. Propagation of such cells in cell culture has become a routine procedure. See Tissue Culture, Academic Press, Kruse and Patterson, editors (1973). Examples of useful host cells are melanoblasts or melanocyte cell lines isolated from pigmented (e.g., PIG3V, melan-a and B16) or albino mice (e.g., melan-c (Bennett, et al. (1989) *Development* 105:379-385).

To create a transgenic non-human animal expressing Grm1, Grm1 nucleic acid sequences are inserted into a germ line of the animal using standard techniques of oocyte microinjection or transfection or microinjection into stem cells. Alternatively, if it is desired replace the endogenous gene, homologous recombination using embryonic stem cells or fetal fibroblasts can be applied.

Mice are often used for transgenic animal models because they are easy to house, relatively inexpensive, and easy to breed. However, other non-human transgenic mammals can also be made in accordance with the present invention such as but not limited to monkeys, sheep, rabbits, dogs and rats. Transgenic animals are those which carry a transgene, that is, a cloned gene introduced and stably incorporated which is passed on to successive generations. In the present invention, the mouse Grm1 was cloned and stably incorporated into the genome of a mouse. In this manner, the specific function of Grm1 is investigated during animal development and initiation of malignancy in order to develop therapeutic strategies.

For oocyte injection, for example in mice, one or more copies of the nucleic acid sequences encoding Grm1 can be inserted into the pronucleus of a just-fertilized mouse oocyte. This oocyte is then reimplanted into a pseudo-pregnant foster mother. The liveborn mice can then be screened for integrants using analysis of tail DNA for the presence of the Grm1 sequences.

Retroviral infection of early embryos can also be performed to insert Grm1 nucleic acid sequences into the transgenic animal. In this method, Grm1 nucleic acid sequences are inserted into a retroviral vector which is used to directly infect embryos during the early stages of development to generate a chimera, some of which lead to germline transmission (Jaenisch (1976) *Proc. Natl. Acad. Sci. USA* 73:1260-1264).

Method of making transgenic mammals are described, e.g., in Wall, et al. (1992) *J. Cell Biochem.* 49(2):113-20; McCreath, et al. (2000) *Nature* 405:1066-1069; Lai, et al. (2002) *Science* 295:1089-92; Hogan, et al. (1986) In: Manipulating the mouse embryo. A Laboratory Manual. Cold Spring Harbor Laboratory Press, Cold Spring Harbor, N.Y.; in WO 91/08216 or U.S. Pat. No. 4,736,866, the disclosure of which is incorporated by reference. It is specifically contemplated that a transgenic animal can be pigmented or albino. For example, a pigmented mouse expressing Grm1 can be generated from C57BL/6J mice or other well-established mouse lines and an albino mouse can be generated from an LAC-MF1 mouse breed. Similarly, the mice disclosed herein can be crossed with a hairless (i.e., not nude or immunodeficient mouse) background so that tumors are visible to facilitate monitoring of tumor growth and development. The present invention encompasses a variety of different methods to create a transgenic non-human animal containing a Grm1 sequence which when expressed in the animal leads to the development of a melanocyte neoplasm. Exemplary methods are described herein but not intended to limit the scope of the invention.

Transgenic animals which express Grm1 in a melanocyte-specific manner can now be made and studied with respect to malignancy and used as a model to study possible therapies including pharmaceutical intervention, gene targeting techniques, antisense therapies, antibody therapies, etc. Furthermore, transgenic in vitro cell lines and melanoma cell lines derived from amelanotic tumor bearing mice can also now be established in accordance with the present invention and also used in order to further elucidate intracellular signaling systems involved in the disease as well as to test and identify potentially therapeutic compounds.

Having identified the optimal conditions for establishing a melanoma cell line which does not require the use of hazardous carcinogens, the present invention is also a method for producing a melanoma cell lines derived from amelanotic tumor bearing animals. The method involves the steps of isolating cells from an amelanotic tumor and culturing the cells in the presence of a Grm1 agonist for a sufficient amount of time to establish cell growth. Desirably, the cells isolated from an amelanotic tumor have been identified as aberrantly overexpressing Grm1 protein. A sample of amelanotic tumor tissue is isolated from a tumor-bearing animal (e.g., a mouse, human, pig, sheep, or cow) and placed on a suitable culture medium containing a Grm1 agonist (e.g., $10^{-3}$ M to $10^{-7}$ M). Suitable Grm1 agonists include, but are not limited to, (RS)-3,5-dihydroxyphenylglycine (DHPG) or quisqualate. When the tumor is from a transgenic animal, the step of culturing the cells can also be carried out in the presence of a means to select for transformed melanocytes cells expressing Grm1 and a selectable marker (e.g., G418 selection). Isolated cells are grown in the presence of the agonist for a period of time sufficient amount for the cells to establish growth such that when the agonist is no longer present in the culture medium the cells remain viable and growth competent. The period of time necessary to achieve viability and growth competence can vary with the host animal from which the tumor cells were isolated and can be in the range of 5 to 15 weeks, or 8 to 10 weeks. Cell lines produced in accordance with this method of the invention are useful for studying tumor growth and development and in assays to identify therapeutic agents which decrease or inhibit tumor growth.

An in vivo assay for identifying an agent which is useful for treating or preventing melanoma associated with Grm1 expression involves the steps of administering a test agent to a Grm1 transgenic animal; and measuring or determining whether the agent decreases or inhibits at least one sign or symptom of melanoma (e.g., lesions on the limbs, pinnae, tail, snout and raised tumors on the eyelid, melanocyte-specific expression of Grm1) which is indicative that the test agent is capable of treating or preventing a melanoma. The results of the screening assay can be compared with a control, e.g., an animal which has not been administered a test agent or an animal which has received an agent known to reduce a sign or symptom of a melanoma. The route of administration of the test agent may vary. Examples of administration routes include, but are not limited, to oral, nasal, rectal, transmucosal, intestinal, parenteral, intravenous, intraperitoneal and topical.

In other embodiments, cell-based assays can be used to identify compounds which modulate expression of nucleic acid sequences encoding Grm1, modulate translation of a Grm1 mRNA, modulate the stability of a Grm1 mRNA or protein, or modulate the activity of the Grm1 protein. The cells used in this assay of the invention can be transgenically modified to express Grm1 from a melanocyte-specific promoter or can be melanoma cell lines known to aberrantly express Grm1. Such an assay involves the steps of contacting a host cell, which overexpresses Grm1 protein, with a test agent; and determining whether the agent inhibits or reduces at least one sign or symptom of melanoma in the host cell. Exemplary signs which can be measured include the level or presence of a Grm1 transcript or level or presence of Grm1 protein or activity (e.g., IP3 accumulation or ERK activation). The level or presence of the Grm1 transcript or protein or protein activity produced in the presence of the test agent can be compared to the level or presence of Grm1 transcript or protein or protein activity produced by the same cell which has not been contacted with the test agent. A decrease in the level of Grm1 or Grm1 activity or the absence of Grm1 or Grm1 activity in the cell contacted with the test agent indicates that the test agent is useful for treating or preventing a melanoma.

Agents which can be screened in accordance with the methods disclosed herein include, agents rationally designed from the crystal structure of Grm1, agents identified in 2 ns molecular dynamics simulations (Costantino, et al. (2002) *J. Comput. Aided Mol. Des.* 16(11):779-84) or identified from a library of test agents using high throughput screening. Test agents of a library can be synthetic or natural compounds. A library can comprise either collections of pure agents or collections of agent mixtures. Pure agents are intended to be interpreted broadly and encompasses organic and inorganic molecules. Organic compounds include, but are not limited to, polypeptides, lipids, carbohydrates, coenzymes, nucleic acid molecules, peptides and small molecules (e.g., having a molecular weight of 200-1000). Polypeptides include but are not limited to antibodies and enzymes. Nucleic acids include but are not limited to DNA, RNA and DNA-RNA chimeric molecules. Suitable RNA molecules include RNAi (e.g., siRNA), antisense RNA molecules and ribozymes. Examples of agent mixtures include, but are not limited to, extracts of prokaryotic or eukaryotic cells and tissues, as well as fermentation broths and cell or tissue culture supernatants or extracts of natural products. In the case of agent mixtures, one may not only identify those crude mixtures that possess the desired activity, but also monitor purification of the active component from the mixture for characterization and development as a therapeutic drug. In particular, the mixture so identified can be sequentially fractionated by methods commonly known to those skilled in the art which may include, but are not limited to, precipitation, centrifugation, filtration, ultrafiltration, selective digestion, extraction, chromatography, electrophoresis or complex formation. Each resulting subfraction can be assayed for the desired activity using the original assay until a pure, biologically active agent is obtained. When a known mixture of compounds (e.g., combinatorial libraries) is used in the assay, further deconvolution can be carried out by preparing smaller mixtures, ultimately resulting in the identification of the active single compound.

Antisense nucleotide sequences that can be used to inhibit the expression of Grm1 include nucleotide sequences that are complementary to nucleotide sequences including, but are not limited to, GENBANK accession number AF320126 (SEQ ID NO:1), NM_000838 (SEQ ID NO:2), HSU31215, HSU31216 or paralogs or orthologs, or portions thereof. Further, an antisense nucleotide sequence can be designed that is specific for an alternatively spliced variant of human Grm1 by directing the antisense nucleotide sequence to nucleic acid sequences specific to the variant of interest.

Those skilled in the art can appreciate that it is not necessary that the antisense nucleotide sequence be fully complementary to the target sequence as long as the degree of sequence similarity is sufficient for the antisense nucleotide sequence to hybridize to its target and reduce production of Grm1 protein (e.g., by at least about 40%, 50%, 60%, 70%, 80%, 90%, 95% or more). As is known in the art, a higher degree of sequence similarity is generally required for short antisense nucleotide sequences, whereas a greater degree of mismatched bases will be tolerated by longer antisense nucleotide sequences.

For example, hybridization of nucleotide sequences can be carried out under conditions of reduced stringency, medium stringency or even stringent conditions (e.g., conditions represented by a wash stringency of 35-40% Formamide with 5× Denhardt's solution, 0.5% SDS and 1×SSPE at 37° C.; conditions represented by a wash stringency of 40-45% Formamide with 5× Denhardt's solution, 0.5% SDS, and 1× SSPE at 42° C.; and/or conditions represented by a wash stringency of 50% Formamide with 5× Denhardt's solution, 0.5% SDS and 1×SSPE at 42° C., respectively). See, e.g., Sambrook et al., *Molecular Cloning, A Laboratory Manual* (2d Ed. 1989) (Cold Spring Harbor Laboratory).

Alternatively stated, antisense nucleotide sequences should have at least about 60%, 70%, 80%, 90%, 95%, 97%, 98% or higher sequence similarity with the complement of the Grm1 coding sequences specifically disclosed herein to reduce the level of Grm1 production.

The length of the antisense nucleotide sequence (i.e., the number of nucleotides therein) is not critical as long as it binds selectively to the intended location and reduces transcription and/or translation of the target sequence, and can be determined in accordance with routine procedures. In general, the antisense nucleotide sequence will be from about eight, ten or twelve nucleotides in length up to about 20, 30, 50, 60 or 70 nucleotides, or longer, in length.

In another embodiment, RNA interference (RNAi) is used to modulate Grm1 expression. RNAi has proven successful in human cells, including human embryonic kidney and HeLa cells (see, e.g., Elbashir, et al. (2001) *Nature* 411:494-8). The mechanism by which RNAi achieves gene silencing has been reviewed in Sharp, et al. (2001) *Genes Dev* 15:485-490; and Hammond, et al. (2001) *Nature Rev. Gen.* 2:110-119). Accordingly, Grm1 expression can be inhibited by introducing into or generating within a cell (i.e., transgenic expression) an siRNA or siRNA-like molecule corresponding to a Grm1-encoding nucleic acid (e.g., SEQ ID NO:1 or SEQ ID NO:2) or fragment thereof, e.g., the siRNA molecule disclosed herein (top strand oligonucleotides template, 5'-GAT CCC GTG GAC GGA GAT GTC ATC ATT TCA AGA GAA TGA TGA CAT CTC CGT CCA TTT TTT GGA AA-3', SEQ ID NO:3 and bottom strand, 5'-GCT TTT CCA AAA AAT GGA CGG AGA TGT CAT CAT TCT CTT GAA ATG ATG ACA TCT CCG TCC ACG G-3', SEQ ID NO:4). An siRNA-like molecule refers to a nucleic acid molecule similar to an siRNA (e.g., in size and structure) and capable of eliciting siRNA activity, i.e., to effect the RNAi-mediated inhibition of expression. In various embodiments, such a method can entail the direct administration of the siRNA or siRNA-like molecule into a cell, or use of the vector-based methods. In one embodiment, the siRNA or siRNA-like molecule is less than about 30 nucleotides in length. In a further embodiment, the siRNA or siRNA-like molecule is about 21-23 nucleotides in length. In another embodiment, an siRNA or siRNA-like molecule is a 19-21 bp duplex portion, each strand having a two nucleotide 3' overhang. In particular embodiments, the siRNA or siRNA-like molecule is substantially identical to an Grm1-encoding nucleic acid or a fragment or variant (or a fragment of a variant) thereof. In other embodiments, the sense strand of the siRNA or siRNA-like molecule is substantially identical Grm1 nucleic acid sequences disclosed herein (RNA having U in place of T residues of the DNA sequence). Kits for production of dsRNA for use in RNAi are available commercially, e.g., from New England Biolabs, Inc. and Ambion Inc. (Austin, Tex., USA). Methods of transfection of dsRNA or plasmids engineered to make dsRNA are routine in the art.

Silencing effects similar to those produced by RNAi have been reported in mammalian cells with transfection of a mRNA-cDNA hybrid construct (Lin, et al. (2001) *Biochem. Biophys. Res. Commun.* 281:639-44), providing yet another strategy for silencing a coding sequence of interest.

In a further embodiment, the agent can be a ribozyme. Ribozyme catalysis has primarily been observed as part of sequence-specific cleavage/ligation reactions involving nucleic acids (Joyce (1989) *Nature* 338:217). For example, U.S. Pat. No. 5,354,855 reports that certain ribozymes can act as endonucleases with a sequence specificity greater than that of known ribonucleases and approaching that of the DNA restriction enzymes. Thus, sequence-specific ribozyme-mediated inhibition of gene expression may be particularly suited to therapeutic applications (Scanlon, et al. (1991) *Proc. Natl. Acad. Sci. USA* 88:10591; Sarver, et al. (1990) *Science* 247:1222; Sioud, et al. (1992) *J. Mol. Biol.* 223:831).

Therefore, in particular embodiments, the invention provides antisense molecules, siRNA or siRNA-like molecules, and ribozymes for exogenous administration to effect the degradation or inhibition of the translation of Grm1 mRNA. Examples of therapeutic antisense oligonucleotide applications, incorporated herein by reference, include: U.S. Pat. Nos. 5,135,917; 5,098,890; 5,087,617; 5,166,195; 5,004,810; 5,194,428; 4,806,463; 5,286,717; 5,276,019 and 5,264,423.

In yet a further embodiment, an agent of the invention can be an antibody or antibody fragment. The antibody or antibody fragment can bind to Grm1 resulting in modulation of Grm1 activity (e.g., as an antagonist). Of particular interest are antagonistic antibodies which bind to and inhibit the activity of Grm1. Suitable antibodies, methods of generating the same, and methods for screening for antagonistic activity are disclosed herein. To illustrate, two antibodies have been generated to the N-terminal amino acids of Grm1 (SEQ ID NO:5) which encompasses the ligand binding region of Grm1 or through rational design or from random screening of peptides from peptide libraries.

Peptide ligands which disrupt or block the activity of Grm1 are further contemplated as exemplary inhibitors of Grm1 activity. These peptide ligands can be generated from sequences of proteins known to bind to Grm1.

Exemplary Grm1 antagonists include small organic molecules with a molecular weight in the range of 200-1000 and are not limited to the (+)-isomer of 3-methyl-5-carboxythyen-2-yl-glycine (3-MATIDA) (Constantino, et al. (2004) Farmaco. 59(2):93-9); antagonists summarized by Gasparini, et al. ((2002) Curr. Opin. Pharmacol. 2(1):43-9); and agents identified in the binding assay for metabotropic glutamate receptors using [$^3$H] L-quisqualic acid and recombinant receptors disclosed by Ohashi, et al. ((2002) Z. Naturforsch [C]. 57(3-4):348-55).

In various embodiments, agents identified in the screening assays of the invention can be used therapeutically in formulations or medicaments to prevent or treat a melanoma. The invention provides corresponding methods of medical treatment, in which a therapeutic dose of a Grm1 inhibitor or antagonist is administered in a pharmacologically acceptable formulation, e.g., to a patient or subject in need thereof. Accordingly, the invention also provides therapeutic compositions containing an agent capable of decreasing Grm1 expression or activity and a pharmacologically acceptable excipient or carrier. In one embodiment, such compositions include a Grm1 inhibitor in a therapeutically or prophylactically effective amount sufficient to treat a melanoma. The therapeutic composition can be soluble in an aqueous solution at a physiologically acceptable pH.

An effective amount refers to an amount effective, at dosages and for periods of time necessary, to achieve the desired therapeutic result, such as a reduction or prevention of a melanoma. A therapeutically effective amount of Grm1 inhibitor may vary according to factors such as the disease state, age, sex, and weight of the individual, and the ability of the agent to elicit a desired response in the individual. Dosage regimens can be adjusted to provide the optimum therapeutic response. A therapeutically effective amount is also one in which any toxic or detrimental effects of the agent are outweighed by the therapeutically beneficial effects. A prophylactically effective amount refers to an amount effective, at dosages and for periods of time necessary, to achieve the desired prophylactic result, such as preventing or inhibiting the rate of angiogenesis or angiogenesis-related disease onset or progression. A prophylactically effective amount can be determined as described above for the therapeutically effective amount. For any particular subject, specific dosage regimens can be adjusted over time according to the individual need and the professional judgement of the person administering or supervising the administration of the compositions.

Agents of the present invention can optionally be administered in conjunction with other therapeutic agents useful in the treatment of a melanoma including dacarbazine, carmustine, lomustine, semustine, fotemustine, cisplatin or carboplatin.

The additional therapeutic agents can optionally be administered concurrently with the agents of the invention. As used herein, the word concurrently means sufficiently close in time to produce a combined effect (that is, concurrently can be simultaneously, or it can be two or more events occurring within a short time period before or after each other).

As used herein, pharmaceutically acceptable carrier or excipient includes any and all solvents, dispersion media, coatings, antibacterial and antifungal agents, isotonic and absorption delaying agents, and the like that are physiologically compatible. In one embodiment, the carrier is suitable for parenteral administration. Alternatively, the carrier can be suitable for intravenous, intraperitoneal, intramuscular, sublingual or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well-known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it is preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, a Grm1 inhibitor or activator can be administered in a time-release formulation, for example in a composition which includes a slow release polymer. The active compounds can be prepared with carriers that protect the agent against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are patented or generally known to those skilled in the art. A generally recognized compendium of such methods and ingredients is Remington: The Science and Practice of Pharmacy, Alfonso R. Gennaro, editor, 20th ed. Lippincott Williams & Wilkins: Philadelphia, Pa., 2000.

As used herein, a melanocyte is a dendritic cell of the epidermis that normally synthesizes tyrosinase and, within its melanosomes, the pigment melanin. However, it is amelanotic melanocyte are also considered a melanocyte in the present invention. A melanocytic neoplasm or malignant melanoma or simply melanoma is intended to mean a tumor arising from the melanocytic system of the skin and other organs. Malignant melanoma has four major subtypes with unique clinical features (see, e.g., Balch, et al. In Cancer: Principles and Practice of Oncology, 4th ed. DeVita, et al. (eds):, pp 1612-1614. Philadelphia, J B Lippincott, 1993). The first major subtype, superficial spreading melanoma, constitutes approximately 70% of melanomas, generally arises in a preexisting nevus. Early in its development, superficial spreading melanoma is a flat lesion with mixtures of deeply pigmented areas and amelanotic foci. As the lesion grows, the surface may become irregular, and the perimeter may show indentation. The second major subtype, nodular melanoma has the second most common pattern of growth (15% to 30%). The lesion is typically blue-black and raised or dome-shaped, and it generally begins in uninvolved skin on the trunk, head, and neck areas. Nodular melanomas are more common in men and tend to arise in middle age. Five percent are amelanotic, and such lesions are frequently misdiagnosed. Nodular melanomas lack the radial growth phase typical of other melanomas and therefore have sharply demarcated borders. They are more aggressive and usually develop more rapidly than do superficial spreading melanomas. Lentigo maligna melanoma, the third subtype, constitutes 4% to 10% of all melanomas. The lesion's propensity to metastasize is small. In general, lentigo maligna melanomas are large (more than 3 cm), tan, flat lesions and are always associated with sun-related changes in the dermis and epidermis. Acral lentiginous melanoma is the fourth type of malignant melanoma. It occurs on the palms or soles or beneath the nail beds. However, not all plantar or solar melanomas are acral lentiginous lesions; a minority are superficial spreading or nodular melanomas. Acral lentiginous melanoma is primarily seen in older patients. Ulceration is commonly observed in this type of melanoma.

There are also three less common types of malignant melanoma which have distinctive clinical presentations and poor prognoses. Desmoplastic melanoma is a melanocyte-derived neoplasm of the skin involving the epidermis but with a predominantly dermal tumor focus. Desmoplastic melanoma lesions are frequently amelanotic, involve deeper structures of the dermis, and have a tendency to track along peripheral nerve sheaths (Jain and Allen (1989) *Am. J. Surg. Pathol.* 13:358-373). Survival is worse than for the common cutaneous melanomas, because dissemination occurs early in the natural history of desmoplastic melanomas. Another less common type of melanoma is uveal (ocular) melanoma, a rare and clinically peculiar type of melanoma arising from the melanocytes of the pigmented uvea. This melanoma is curable when detected at an early stage. It may be observed when quite small, but at this stage is difficult to distinguish clinically from a benign nevus. Uveal melanoma generally presents at an advanced stage and has an extremely poor prognosis with a propensity to metastasize to the liver (Shields (1993) *Cancer* 72:2067-2068). The third clinically distinctive type of melanoma is the mucosal variant, which can arise in the mouth, anus, external or internal genital tract, upper respiratory tract, or elsewhere in the gastrointestinal tract. It also tends to present as advanced local disease and has an aggressive natural history leading to death. Thus, methods for early detection and diagnosis of this melanoma as well as other types of malignant melanoma can increase the survival rate of a patient with the disease as treatment of the melanoma can begin early in the development of the tumor.

Accordingly, in another embodiment of the present invention, Grm1 is used as a marker for early detection and diagnosis of a melanoma in a patient. As the presence or increased amount of Grm1 mRNA or Grm1 protein in a cell is indicative of a predisposition to melanoma development, the diagnostic method of the invention is intended to include the detection of either an RNA transcript encoding Grm1 or a Grm1 protein. In general, an assay for detecting Grm1 includes isolating a sample such as a biopsy sample, tissue, or cell from a subject having or suspected of having a melanoma and detecting the presence or amount of Grm1 RNA transcript or protein in the sample as compared to a control. A subject having or suspected of having a melanoma includes an individual having certain phenotypic factors which increase the risk for the development of malignant melanoma. These factors include blue, green, or gray eyes; blond or red hair; light complexion; freckles; sun sensitivity; and the tendency to burn rather than tan. Other significant risk factors include a family history of melanoma, a personal history of non-melanoma skin cancer, an increased number of melanocytic nevi, and xeroderma pigmentosum. Subjects who have had one malignant melanoma are also at increased risk for developing another. Malignant melanoma should be suspected in any pigmented skin or mucosal surface lesion that changes in color or size, begins to itch, or bleeds spontaneously. The clinical characteristics that suggest malignancy include variegation in color; acquisition of red, white, or blue color in a previously brown or black lesion; border irregularity; and surface elevation (Wick, et al: (1980) *Cancer* 45:2684-2686).

To detect an RNA transcript encoding Grm1, nucleic acids can be isolated from the sample or alternatively can be prepared following microdissection of the tumor in order to isolate tumor cells from the normal cells present in the sample. The nucleic acid can be whole cell RNA or fractionated to Poly-A+. It may be desired to convert the RNA to a complementary DNA (cDNA). Normally, the nucleic acid is amplified. Methods for isolating, fractionating and amplifying nucleic acids from samples is well-known in the art. See, e.g., Sambrook and Russell (2001) supra and other standard laboratory molecular biology protocol manuals.

A variety of methods can be used to evaluate or quantitate the level of Grm1 RNA transcript present in the sample. For example, levels of Grm1 RNA transcript can be evaluated using well-known methods such as northern blot analysis (see, e.g., Sambrook and Russell (2001) supra); oligonucleotide or cDNA fragment hybridization wherein the oligonucleotide or cDNA is configured in an array on a chip or wafer; RNase protection analysis; or RT-PCR, as exemplified herein.

Suitable primers, probes, or oligonucleotides useful for such detection methods are exemplified herein or can be generated by the skilled artisan from the sequence provided as GENBANK accession number AF320126 (SEQ ID NO:1), NM_000838 (SEQ ID NO:2), HSU31215, HSU31216 or paralogs or orthologs thereof. The term primer, as defined herein, is meant to encompass any nucleic acid that is capable of priming the synthesis of a nascent nucleic acid in a template-dependent process. Typically, primers are oligonucleotides from ten to twenty-five base pairs in length, but longer sequences can be employed. Primers can be provided in double-stranded or single-stranded form. Probes are defined differently, although they can act as primers. Probes, while perhaps capable of priming, are designed for hybridizing to the target DNA or RNA and need not be used in an amplification process. In particular embodiments, the probes or primers are labeled with, for example, radioactive species ($^{32}P$, $^{14}C$, $^{35}S$, $^{3}H$, or other label) or a fluorophore (rhodamine, fluorescein). Depending on the application, the probes or primers can be used cold, i.e., unlabeled, and the RNA or cDNA molecules are labeled.

Various RT-PCR methodologies can be employed to evaluate the level of Grm1 RNA transcript present in a sample. As clinical samples are of variable quantity and quality a relative quantitative RT-PCR reaction can be performed with an internal standard. The internal standard can be an amplifiable cDNA fragment that is larger than the target cDNA fragment and in which the abundance of the mRNA encoding the internal standard is roughly 5-100 fold higher than the mRNA encoding the target. This assay measures relative abundance, not absolute abundance of the respective mRNA species.

Other assays can be performed using a more conventional relative quantitative RT-PCR assay with an external standard protocol. These assays sample the PCR products in the linear portion of their amplification curves. The number of PCR cycles that are optimal for sampling must be empirically determined for each target cDNA fragment. In addition, the reverse transcriptase products of each RNA population isolated from the various samples must be carefully normalized for equal concentrations of amplifiable cDNAs. This consideration is very important since the assay measures absolute mRNA abundance. Absolute mRNA abundance can be used as a measure of differential gene expression only in normalized samples. While empirical determination of the linear range of the amplification curve and normalization of cDNA preparations are tedious and time consuming processes, the resulting RT-PCR assays can be superior to those derived from the relative quantitative RT-PCR assay with an internal standard.

Specifically contemplated by the present invention are chip-based DNA technologies. Briefly, these techniques involve quantitative methods for analyzing large numbers of genes rapidly and accurately. By tagging genes with oligonucleotides or using fixed probe arrays, one can employ chip technology to segregate target molecules as high density arrays and screen these molecules on the basis of hybridization (see, e.g., Pease, et al. (1994) *Proc. Natl. Acad. Sci. USA* 91(11):5022-6; Fodor, et al. (1991) *Science* 251(4995): 767-73).

Depending on the format, detection can be performed by visual means (e.g., ethidium bromide staining of a gel). Alternatively, detection can involve indirect identification of the product via chemiluminescence, radiolabel or fluorescent label or even via a system using electrical or thermal impulse signals (Bellus (1994) *J. Macromol. Sci. Pure Appl. Chem.* A311:1355-1376).

In an alternative embodiment, Grm1 protein is detected in a sample. In general, the detection of Grm1 protein is carried out by immunoassays using antibodies which specifically bind to Grm1. Antibodies which specifically bind Grm1 can be either polyclonal or monoclonal. Moreover, such antibodies can be natural or partially or wholly synthetically produced. All fragments or derivatives thereof which maintain the ability to specifically bind to Grm1 protein are also included. The antibodies can be a member of any immunoglobulin class, including any of the human classes: IgG, IgM, IgA, IgD, and IgE.

Antibody fragments can be any derivative of an antibody which is less than full-length. In general, an antibody fragment retains at least a significant portion of the full-length antibody's specific binding ability. Examples of antibody fragments include, but are not limited to, Fab, Fab', F(ab')$_2$, scFv, Fv, diabody, or Fd fragments. The antibody fragment can be produced by any means. For instance, the antibody fragment can be enzymatically or chemically produced by fragmentation of an intact antibody or it can be recombinantly produced from a gene encoding the partial antibody sequence. The antibody fragment can optionally be a single-chain antibody fragment. Alternatively, the fragment can be multiple chains which are linked together, for instance, by disulfide linkages. The fragment can also optionally be a multi-molecular complex. A functional antibody fragment typically contains at least about 50 amino acids and more typically contains at least about 200 amino acids.

An antibody for use in the methods of the present invention can be generated using classical cloning and cell fusion techniques. For example, the antigen of interest is typically administered (e.g., intraperitoneal injection) to wild-type or inbred mice (e.g., BALB/c) or transgenic mice which produce desired antibodies, or rats, rabbits or other animal species which can produce native or human antibodies. The antigen can be administered alone, or mixed with adjuvant, or expressed from a vector (VEE replicon vector), or as DNA, or as a fusion protein to induce an immune response. Fusion proteins contain the peptide against which an immune response is desired coupled to carrier proteins, such as histidine tag (his), mouse IgG2a Fc domain, β-galactosidase, glutathione S-transferase, keyhole limpet hemocyanin (KLH), or bovine serum albumin, to name a few. In these cases, the peptides serve as haptens with the carrier proteins. After the animal is boosted, for example, two or more times, the spleen is removed and splenocytes are extracted and fused with myeloma cells using the well-known processes (Kohler and Milstein (1975) *Nature* 256:495-497; Harlow and Lane (1988) Antibodies: A Laboratory Manual, Cold Spring Harbor Laboratory, New York). The resulting hybrid cells are then cloned in the conventional manner, e.g., using limiting dilution, and the resulting clones, which produce the desired monoclonal antibodies, are cultured.

Alternatively, antibodies which specifically bind Grm1 are produced by a phage display method. Methods of producing phage display antibodies are well-known in the art (e.g., Huse, et al. (1989) *Science* 246(4935):1275-81).

Selection of Grm1-specific antibodies is based on binding affinity and can be determined by various well-known immunoassays including, enzyme-linked immunosorbent, immunodiffusion chemiluminescent, immunofluorescent, immunohistochemical, radioimmunoassay, agglutination, complement fixation, immunoelectrophoresis, and immunoprecipitation assays and the like which can be performed in vitro, in vivo or in situ. Such standard techniques are well-known to those of skill in the art (see, e.g., "Methods in Immunodiagnosis", 2nd Edition, Rose and Bigazzi, eds. John Wiley & Sons, 1980; Campbell et al., "Methods and Immunology", W. A. Benjamin, Inc., 1964; and Oellerich, M. (1984) *J. Clin. Chem. Clin. Biochem.* 22:895-904). Suitable anti-Grm1 antibodies are disclosed herein and in U.S. Pat. No. 5,869,609, incorporated herein by reference. Antagonistic antibodies can also be used for detecting Grm1.

Anti-Grm1 antibodies can be used in diagnostic, prognostic, or predictive methods to evaluate the level or presence or absence of Grm1 in healthy and diseased tissues via techniques such as ELISA, western blotting, or immunohistochemistry. The general method for detecting Grm1 provides contacting a sample with an antibody which specifically binds Grm1. The antibody is allowed to bind to Grm1 to form an antibody-antigen complex. The conditions and time required to form the antibody-antigen complex may vary and are dependent on the sample being tested and the method of detection being used. Once non-specific interactions are removed by, for example, washing the sample, the antibody-antigen complex is detected using any one of the immunoassays described above as well a number of well-known immunoassays used to detect and/or quantitate antigens (see, for example, Harlow and Lane (1988) supra). Such well-known immunoassays include antibody capture assays, antigen capture assays, and two-antibody sandwich assays.

Immunoassays typically rely on labeled antigens, antibodies, or secondary reagents for detection. These proteins may be labeled with radioactive compounds, enzymes, biotin, or fluorochromes. Of these, radioactive labeling may be used for almost all types of assays. Enzyme-conjugated labels are particularly useful when radioactivity must be avoided or when quick results are needed. Biotin-coupled reagents usually are detected with labeled streptavidin. Streptavidin binds tightly and quickly to biotin and may be labeled with radioisotopes or enzymes. Fluorochromes, although requiring expensive equipment for their use, provide a very sensitive method of detection. Those of ordinary skill in the art will know of other suitable labels which may be employed in accordance with the present invention. The binding of these labels to antibodies or fragments thereof may be accomplished using standard techniques (e.g., Kennedy, et al. (1976) Clin. Chim. Acta 70:1-31; Schurs, et al. (1977) Clin. Chim Acta 81:1-40) and methods of detecting these labels are also well-known to the skilled artisan.

After detecting the level, presence or absence of Grm1 transcript or Grm1 protein present in a sample, the results seen in a given subject can be compared with a known standard. A known standard is a statistically significant reference group of normal subjects or subjects that have cancer to provide diagnostic, prognostic, or predictive information pertaining the subject from whom the sample was obtained. The standard can be generated by performing prognostic analyses of multiple tumor samples derived from multiple subtypes of melanomas.

The diagnostic method of the invention can be used alone or in combination with other well-known diagnostic or staging methods for melanomas. For example, microstaging allows prognostic categorization of risk of relapse and survival. Tumor thickness is an important prognostic factor for patients with malignant melanoma limited to the primary site. Clark's levels of microinvasion reflect increasing depth of tumor penetration into the dermal layers and the subcutaneous fat (Clark, et al: (1969) Cancer Res. 29:705-726). In Breslow's microstaging system, the thickness of the lesion is measured with an ocular micrometer to determine the maximal vertical thickness of the melanoma (Breslow (1975) Ann. Surg. 182:572-575). Both systems are predictive of the risk of metastasis. Two staging systems are commonly used for malignant melanoma. A simple and widely used three-stage system developed by the World Health Organization (WHO) categorizes patients on the basis of nodal and distant metastasis (Goldsmith (1979) Cancer J. Clin. 29:194). The American Joint Committee on Cancer (AJCC) has a four-stage system incorporating tumor thickness as part of the staging criteria and dividing clinically localized melanomas into two stages according to the microstaging information.

The present invention also provides a kit which is useful for carrying out the diagnostic method of the present invention. The kit generally contains a container containing an antibody which specifically binds Grm1. The kit also contains other solutions necessary or convenient for carrying out the invention. The container can be made of glass, plastic or foil and can be a vial, bottle, pouch, tube, bag, etc. The kit can also contain written information, such as procedures for carrying out the present invention; analytical information, such as the amount of reagent contained in the first container; or data describing the correlation between the presence of Grm1 protein in a sample and the presence of a melanoma. The container can further be in another container, e.g., a box or a bag, along with the written information.

The invention is described in greater detail by the following non-limiting examples.

EXAMPLE 1

Western Blot Analysis

Using a Polytron (Brinkmann Instruments, Westbury, N.Y.), pinnae, brain and tail tissues were lysed at 4° C. in lysis buffer (50 mM Tris-HCl, 150 mM NaCl, 1 mM EDTA, 1% NONIDET-P40, 5% glycerol and 1 mM dithiothreitol, pH 7.4) in the presence of protease inhibitors (Complete protease inhibitor cocktail tablets, Roche Applied Science, Indianapolis, Ind.). Cells were lysed in the same buffer. Protein concentration of each sample was determined with BIO-RAD DC Protein Assay (BIO-RAD Laboratories, Hercules, Calif.). Protein samples were loaded into each lane of a 7.5% polyacrylamide gel along with prestained molecular weight markers (BIO-RAD). After transfer of proteins onto nitrocellulose membranes (Osmonics, Minnetonka, Minn.), the membranes were probed with a rabbit polyclonal antibody against Grm1 at 2 µg/mL (Upstate Biotechnology, Lake Placid, N.Y.) and, for the normalization experiments, also with a mouse monoclonal antibody against tubulin at 2 µg/mL (Santa Cruz Biotechnology, Santa Cruz, Calif.). Protein bands were visualized with the Amersham ECL system (Amersham Pharmacia Biotech, Ltd., Uppsala, Sweden). In addition, antibodies to peptides derived from Rab32 and Shprh were raised and affinity-purified using standard methods

EXAMPLE 2

RT-PCR

For RNA analysis, cDNA synthesis and PCR, total RNA was purified from tissue samples with TRI REAGENT (Molecular Research Center, Cincinnati, Ohio). Oligo-dT-primed, first-strand cDNA was generated from total RNA with SuperScript-II RNase H⁻ Reverse Transcriptase (IN-VITROGEN Corporation, Carlsbad, Calif.) and PCR was completed using the Taq PCR Master Mix Kit (QIAGEN, Inc., Valencia, Calif.), according to manufacturers' protocols. Guided by pilot reactions to obtain relatively equivalent levels of RT-PCR product from Tyrp1 or Dct transcripts (using Tyrp1 or Dct primers, respectively), the amount of melanocyte cDNA input into the final duplex PCR reaction was standardized. Tyrp1 primers used were: Trp1A 5'-CTT TCT CCC TTC CTT ACT GG-3' (SEQ ID NO:6) and Trp1B 5'-TGG CTT CAT TCT TGG TGC TT-3' (SEQ ID NO:7). Primers for amplifying Dct2 (i.e., Trp2) were: HuTrp2A-1022F 5'-ACA TTA TTA GGA CCA GGA CGC CC-3' (SEQ ID NO:8) and HuTrp2B-1775R 5'-GAA ACT GGC AGA TCG ATG GCA TAG C-3' (SEQ ID NO:9). RT-PCR reactions were carried out using primers from Grm1 and either Tyrp1 or Dct. Primers for amplifying human Grm1 were: huglu965F 5'-GGA GAG CGG AAT GGA CGC TT-3' huglu2084R 5'-ACC ACT GGT GTG TCC CGG TA-3' (SEQ ID NO:11) and Grm1 primers were: Glu5'D1 5'-CCG AGA GCG GCT TCC CAA G-3' (SEQ ID NO:12) and Glu3'17R 5'-AGA TTC CTG CCG TCA ATG GG-3' (SEQ ID NO:13).

EXAMPLE 3

Transgenic Constructs

The construct used for microinjection contained a ~3600-bp MspA11-StuI fragment of the Dct promoter (Budd and Jackson (1995) supra), from −3239 to approximately +447 which corresponds to sequences 1 to 3686 of GENBANK accession number X85126 (SEQ ID NO:14), adjacent to the Grm1 coding sequence (SEQ ID NO:1) followed by the human growth hormone poly-A (Jhappan, et al. (1990) Cell 61:1137-1146) (SEQ ID NO:15) cloned into pBSK(+). The Grm1 sequence included 241 bp of Grm1 intron 1 sequence and transcribed sequences corresponding to −105 to +4164. After double cesium chloride plasmid purification and excision from the plasmid by NotI, the insert was gel-purified and injected into the pronuclei of C57BL/6J mice.

For Dct-Grm1 genotyping, DNA was extracted from tail biopsies using standard techniques and then analyzed by a duplex PCR procedure using both Grm1 primers and Rapsn control primers. Offspring were subsequently obtained from each of the three positive founder lines.

PKC wild-type or kinase-negative isoform adenoviruses are known in the art (Oka, et al. (2002) supra). Mouse melanoma cell lines were infected for 12 hours with adenovirus encoding the desired PKC isoform and control GFP, in RPMI-glu with 2% dialyzed fetal calf serum, followed by overnight serum starvation. Cells were viewed by using a Zeiss microscope prior to agonist treatment.

EXAMPLE 4

Immunofluorescence

Immunofluorescence analysis was conducted on 5 μm-thick paraffin-embedded sections of mouse lymph nodes. After removing the paraffin, hydrating and steaming the sections in Antigen Unmasking Solution (Vector Laboratories, Burlingame, Calif.) for 30 minutes, the sections were blocked with 5% goat serum in phosphate-buffered saline and subsequently incubated with rabbit polyclonal antiserum against Tyrp1 α-PEP-1 (dilution 1:1000) overnight at 4° C. The sections were then incubated with Cy5-conjugated goat antibody against rabbit IgG (1:1000; Jackson Immunoresearch Laboratories, Inc. West Grove, Pa.) for 1 hour at room temperature and images were collected using a ZEISS Axiophot microscope equipped with a 12-bit CCD camera.

To conduct immunofluorescence analysis of tumor cell lines, cells were plated on coverslips in 60-mm tissue culture plates. At 70% confluence, the cells were fixed in methanol/acetone (1:1) for 5 minutes, rinsed in phosphate-buffered saline (PBS), and incubated for 45 minutes at room temperature with the rabbit anti-Grm1 polyclonal antibody μg/mL; Upstate Biotechnology, Waltham, Mass.) and a goat anti-Dct antibody (5 μg/mL; Santa Cruz Biotechnology, Santa Cruz, Calif.). Incubation with secondary antibodies, TEXAS RED® dye-conjugated anti-rabbit antibody (Cortex Biochem, San Leandro, Calif.) and ALEXAFLUOR® 488 dye-conjugated anti-goat antibody (Molecular Probes, Eugene, Oreg.), were performed for one hour at room temperature, followed by washing and mounting. Cells were viewed using a Zeiss microscope.

EXAMPLE 5

Isolation and Growth of Melanoma Cell Lines

Ear tumors were excised from independent mice and cut in half. Western blot analysis of Grm1 expression was performed on one half of the tumor and the other half was minced and allowed to establish in culture in RPMI 1640 containing 10% fetal bovine serum at 37° C. in a 10% $CO_2$ atmosphere. Melanocytes were gently selected by incubation of cells with genetecin (75-150 μM) for 3-4 days and growth on $10^{-5}$ M quisqualate for about 8 weeks. Expression of melanocyte markers and Grm1 in these cultured cells was later confirmed by immunofluorescence.

To have a minimum amount of the natural ligand (glutamate) present in the growth medium, customized glutamine- and glutamate-free RPMI (RPMI-glu) was used (INVITROGEN™, Carlsbad, Calif.). GLUTAMAX™ (INVITROGEN™), a substitute for glutamate and glutamine, was added to the growth medium at a final concentration of 2 mM, and 10% dialyzed fetal calf serum (INVITROGEN™) was used to supplement the medium. For induction with Grm1 agonist, quisqualate, the cells were grown in RPMI-glu for 3-4 days, plated at $3 \times 10^5$ cells per 60-mm plate and serum starved overnight. Several concentrations of quisqualate ($10^{-4}$ M to $10^{-6}$ M) and several time points (30 seconds to 120 minutes) were tested for optimal induction. For Grm1 antagonist effects, cells were pretreated for 30 minutes with $10^{-5}$ M of LY367385 before agonist treatment. For PKC inhibitor (RO-31-8220) and calcium chelators (EGTA, BAPTA-AM), cells were pretreated for indicated times before agonist challenge.

EXAMPLE 6

IP3 Accumulation

Cells were plated in 24-well plates and grown in glutamate and inositol-free RPMI supplemented with 10% dialyzed fetal bovine serum. Cells were then serum starved for 18 hours. Assays for quisqualate-induced IP3 accumulation were performed on cells treated with $^3$H-inositol (5 μCi/mL) according to standard methods (Thandi, et al. (2002) J. Neurochem. 83(5):1139-53).

EXAMPLE 7

Dominant-Negative Grm1

Dominant negative constructs of Grm1 are well-known in the art (Francesconi, et al. (1998) supra). For IP3 accumulation experiments, cells were transfected for 6 hours with 0.5 μg of DNA per well with DOTAP reagent (Roche, Indianapolis, Ind.) 24 hours before agonist challenge. Expression of dominant-negative form of Grm1 was confirmed by western blot analysis. For phospho-ERK1/2 immunoblots, 0.5 to 2.5 μg of dominant-negative Grm1 was transfected 24 hours prior to agonist treatment.

EXAMPLE 8

MTT Assay

Cells were plated in 96-well plates at $10^3$ cells per well in RPMI supplemented with 10% FBS in the presence or absence of TPA. MTT-based colorimetric assay was carried out for different time periods and were assayed in a plate reader according to manufacturer's instructions (Roche Diagnostics, Indianapolis, Ind.).

EXAMPLE 9

In Vivo Tumorigenicity Assay

Cells ($10^7$) were injected subcutaneously into both sides of the animals. Animals were checked twice a week for tumor development.

EXAMPLE 10

Cell Line Lysate Preparation

Proteins were extracted using lysis buffer (50 mM Tris-HCl, 150 mM NaCl, 1 mM EDTA, 1% NP-40, 5% glycerol, and 1 mM dithiothreitol, pH 7.4) and protease inhibitors (Complete protease inhibitor cocktail tablets, Roche Molecular Biochemicals, Indianapolis, Ind.). Protein concentrations were measured using the BIO-RAD® DC Protein Assay kit (Bio-Rad, Hercules, Calif.). Equal amounts of lysates were loaded in each lane in 7.5 or 10% polyacrylamide gels (BIO-RAD®, Hercules, Calif.). Proteins were transferred to nitrocellulose membranes (Osmonics, Minnetonka, Minn.). Ponceau Red staining of membranes, after transfer, was performed to verify equivalent amounts of protein between samples. Anti-PERK, ERK, PhosphoPKC isoforms, PKC isoforms antibodies were obtained from Cell Signaling Technology, Inc. (Beverly, Mass.).

What is claimed is:

1. A transgenic mouse whose genome comprises a transgene including the coding sequence of SEQ ID NO:1 encoding a metabotropic glutamate receptor 1 operably linked to the melanocyte-specific promoter of SEQ ID NO:14, wherein said transgenic mouse expresses the metabotropic glutamate receptor 1 in melanocytes, develops lesions on hairless skin, and lacks pigmentation.

* * * * *